US007695931B2

(12) United States Patent
Nishida et al.

(10) Patent No.: US 7,695,931 B2
(45) Date of Patent: Apr. 13, 2010

(54) CAROTENOID HYDROXYLASE GENE, METHOD FOR PREPARING HYDROXYLATED CAROTENOID, AND NOVEL GERANYLGERANYL PYROPHOSPHATE SYNTHASE

(75) Inventors: Yasuhiro Nishida, Nakaniikawa-gun (JP); Kyoko Adachi, Kamaishi (JP); Hiroaki Kasai, Kamaishi (JP); Yoshikazu Shizuri, Kamaishi (JP); Sadao Komemushi, Osaka (JP); Norihiko Misawa, Kamaishi (JP)

(73) Assignee: Kirin Holdings Kabushiki Kaisha, Tokyo (JP)

( * ) Notice: Subject to any disclaimer, the term of this patent is extended or adjusted under 35 U.S.C. 154(b) by 608 days.

(21) Appl. No.: 10/579,338

(22) PCT Filed: Nov. 4, 2004

(86) PCT No.: PCT/JP2004/016297

§ 371 (c)(1),
(2), (4) Date: May 15, 2006

(87) PCT Pub. No.: WO2005/049643

PCT Pub. Date: Jun. 2, 2005

(65) Prior Publication Data
US 2007/0148727 A1     Jun. 28, 2007

(30) Foreign Application Priority Data
Nov. 18, 2003 (JP) .............................. 2003-388165
Jun. 3, 2004 (JP) .............................. 2004-165919

(51) Int. Cl.
C12P 23/00 (2006.01)
C12N 9/02 (2006.01)
C12N 1/20 (2006.01)
C12N 15/74 (2006.01)
C12P 21/06 (2006.01)
C12P 19/34 (2006.01)
C07H 21/04 (2006.01)

(52) U.S. Cl. ..................... 435/67; 435/189; 435/183; 435/252.33; 435/69.1; 435/91.1; 435/488; 536/23.2; 536/23.7

(58) Field of Classification Search .................. None
See application file for complete search history.

(56) References Cited

U.S. PATENT DOCUMENTS
5,429,939 A     7/1995 Misawa et al.
2004/0078846 A1     4/2004 Desouza et al.

FOREIGN PATENT DOCUMENTS

WO WO-2002/79395 A2 10/2002

WO WO-2005/118812 A1 12/2005

OTHER PUBLICATIONS

Tao et al., A carotenoid synthesis gene cluster from a non-marine Brevundimonas that synthesiszes hydroxylated astaxanthin. Gene, 2006, vol. 379: 101-108. Published online May 5, 2006.*
Whisstock et al., Prediction of protein function from protein sequence. Q. Rev. Biophysics., 2003, vol. 36 (3): 307-340.*
Broun et al., Catalytic plasticity of fatty acid modification enzymes underlying chemical diversity of plant lipids. Science, 1998, vol. 282: 1315-1317.*
Witkowski et al., Conversion of b-ketoacyl synthase to a malonyl decarboxylase by replacemnt of the active-site cysteine with glutamine. Biochemistry, 1999, vol. 38: 11643-11650.*
Seffernick et al., Melamine deaminase and Atrazine chlorohydrolase: 98 percent identical but functionally different. J. Bacteriol.,2001, vol. 183 (8): 2405-2410.*
Guo et al., Protein tolerance to random amino acid change. PNAS., 2004, vol. 101 (25): 9205-9210.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Nishida et al., Applied and Environmental Microbiology, vol. 71, No. 8, pp. 4286-4296 (Aug. 2005).
Choi et al., Appl. Microbiol. Biotechnol., vol. 72, No. 6, pp. 1238-1246 (Oct. 2006).
Norihiko Misawa et al.; Journal of Bacteriology, vol. 172, No. 12, pp. 6704-6712 (Dec. 1990).
Norihiko Misawa et al.; Journal of Bacteriology, vol. 177, No. 22, pp. 6575-6584 ( Nov. 1995).
Gerhard Sandmann et al.; FEMS Microbiology Letters, 90, pp. 253-258 (1992).
Foss, P. et al.; Acta Chemica Scandinavica, vol. B40, pp. 157-162 (1986).
Yasuhiro Nishida et al., Japanese Society for Marine Biotechnology Taikai Koen Yoshishu, Jun. 17, 2004, vol. 7, p. 150, AP-4.
Yokoyama A. et al., Biosci. Biotech. Biochem., 1996, vol. 60, No. 2, pp. 200 to 203.
William C. et al., PNAS, 2001, vol. 98, pp. 4136 to 4141.
P.D. Fraser et al., J. Biol. Chem. 1997, vol. 272, pp. 6128 to 6135.

* cited by examiner

Primary Examiner—Ganapathirama Raghu
(74) Attorney, Agent, or Firm—Birch, Stewart, Kolasch & Birch LLP

(57) ABSTRACT

The present invention provides a *Brevundimonas* sp. strain SD212-derived peptide having β-ionone ring-2-hydroxylase activity and a gene encoding the same, to thereby make it possible to produce rare carotenoids in which a hydroxyl group is introduced at the position 2(2') carbon in their β-ionone ring in large quantities.

The present invention also provides a novel gene encoding an enzyme which introduces a hydroxyl group at the position 3(3') carbon in the β-ionone ring of carotenoids, and a novel gene encoding a geranylgeranyl pyrophosphate synthase.

11 Claims, 10 Drawing Sheets

SEQUENCE LISTING

<160> NUMBER OF SEQ ID NOS: 38

<210> SEQ ID NO 1
<211> LENGTH: 519
<212> TYPE: DNA
<213> ORGANISM: Brevundimonas sp.

<400> SEQUENCE: 1

```
ttcgatgcgg ggccgacggt catcaccgat ccttcggcgc tggaggagct gttcgagggc      60
gcggggcgca agctgtcgga ctatgtcgaa ctgctgccgg tcgccccctt ctatcggctg     120
tgctgggaag acggcgacgt cttcgactac gtcaacggcc aggacgagct ggaccgccag     180
atcgtcgccc gcaacccggc cgacaaggag ggctatcgcc ggttcctggc ctattcccag     240
gacctgctga aggaaggcta tctgaagctg ggcgccgtgc cctttctgga cttcgccagc     300
atggtcaagg cggcgccgga gttgatgcgg ctccaggcct gcggtcggt ctatgacaag      360
gtcgccggct atatccagga cgagcatctg cgtcaggcct tcagctttca ctccctgctg     420
gtgggcggca atccgttcgc cacctcatcg atctacgccc tgatccacgc gctggagcgg     480
cgctggggcg tctggttccc gcgcggcggc accggcgcc                            519
```

<210> SEQ ID NO 2
<211> LENGTH: 11991
<212> TYPE: DNA
<213> ORGANISM: Brevundimonas sp.
<220> FEATURE:
<221> NAME/KEY: CDS
<222> LOCATION: (10748)..(11518)

<400> SEQUENCE: 2

```
gaattccccg tgaagatgcg gggttcccgc ggtcagacgg aaagacccta tgaacctta     60
ctatagcttc gccttggcgt tagcgaccgt atgtgtagga taggtgggag actatgaaac   120
cggggcgcca gctctggtgg agtcgtcctt gaaataccac ccttactgtc gttgacgtct   180
aaccgaggac cgttatccgg tcccgggaca tggcgtggtg ggtagtttga ctggggcggt   240
cgcctcccaa agtgtaacgg aggcgcgcga tggtgagctc agagcggtcg gaaatcgctc   300
gtcgagtgca atggcataag ctcgcctgac tgcgagactg acaagtcgag cagagacgaa   360
agtcggccat agtgatccgg tggtcccgag tggaagggcc atcgctcaac ggataaaagg   420
tactctaggg ataacaggct gattttgccc aagagtccat atcgacggca agtttggca    480
cctcgatgtc ggctcatcac atcctggggc tggagcaggt cccaagggta tggctgttcg   540
ccatttaaag tggtacgtga gctgggttca aacgtcgtg agacagttttg gtccctatct   600
gccgtgggtg ttcgaagctt gagaggatct gtccctagta cgagaggacc gggatggaca   660
tacctctggt gtacctgtca tggcgccagc tgtgcagcag ggtagctaag tatgaatag    720
ataaccgctg aaagcatcta agcgggaaac taacctcaaa acaaggcttc gctgaggatc   780
gtggaagact accacgttga taggccaggt gtggaagcgc ggcgacgcgt gaagcttact   840
ggtactaata atccgatcgg tttgatcgtt tctcagcaaa actcattcga tgatcatcaa   900
tgacccgatg atcgtcacga caatgtcttc tcatcatccg ctgtccgcct cgttgacctg   960
gtggctatgt cggaggttcc ccacccgatc ccattccgaa ctcggtcgtt aagccctcca  1020
gagccaatgg tacttcgtct caaggcgcgc gagagtaggt cgccgccggg tctaccaggc  1080
ggacagccga tgatgaaaaa cctatcgaac ccttcttcct ccacaaacca cccctgccgc  1140
```

-continued

| | |
|---|---|
| gggatggagc agcccggtag ctcgtcaggc tcataacctg aaggtcgcag gttcaaatcc | 1200 |
| tgctcccgca cccaaacaat caagccgctg gatcaacgat ccagcggctt tttgctgcct | 1260 |
| gaaccccaa gcccgcgccc ccatcccgga cccgaacgcc aagcgtcggc tctcaaggag | 1320 |
| tgaactggat cgtatgttcg aacgggcggt cgatcgggcg gccgccgtcg cgcgaggggg | 1380 |
| gcgtcgcggt tccgttcatc agggccacag ccgcctcgcc gaacccgtag cccgacggc | 1440 |
| tctccgacag cacgacgcaa tccgagaccc ggccgtcggc acgcccaatg catcgcagtc | 1500 |
| gaaccctgac gtcgtccaag acgggcgctg aggattgggc ggccgccttg atcccgccgg | 1560 |
| acgtcttggg ctgcgccttg gccggatcgg cggcgggcgc cggcgtcgaa ctgagggcgg | 1620 |
| caagagcgaa cagcagggcg aggggcatgg gccatttcct tctcacctat aaggcccgga | 1680 |
| acgccgccgt gttcccttcg ccgacacaaa ggtcgccgaa caggcgttcg gcggcccgca | 1740 |
| agcagccttg gatcaagact cgccgcgcca caaacgccac cagggccgcc aggggtgag | 1800 |
| gtggtgttcg tggtggcggc cgaagtgaaa gcaggtgagc agggaaagaa cggggccgta | 1860 |
| gccgctgctg cgggcgtggt gggcgtcggc gaacggctgg tcggtgtggc ggtgcggcag | 1920 |
| ccaggtgccg aaggtgaaga gctgaagcgc tgaaagcagg gccggcgcgg cccagaaggt | 1980 |
| caggagattg gccggccgcg ccccaggcc gaagagggcg atcaggacca gggcggtcag | 2040 |
| gaccgccatc tcgcgccagc cgaaataggt gcgaaagaag ttcaggaacc agggaaggaa | 2100 |
| ggcgcggggc gccggggcgt aaaagtccgg gtcgtcggcc gtgccgggcg cggcgtggtg | 2160 |
| ggcgtggtgc gccgtcttca gccgatcgaa gcggaagccc gcatagagcc ccagggtcag | 2220 |
| ccggccgact gcggcgttca gccgcggccg tcccggcgcc agggagccgt gcatggcgtc | 2280 |
| atgggcgacg atgaaaaggc cgaccgacaa ccaggtctgg accgctacga tcgccgggac | 2340 |
| gatcaccaga ctggaggtgc cccagcggtg aaaatagacg ccgtagacgt gcaggctccc | 2400 |
| ccatcccgcc acgatcattc ccgccagggt cagaccgatc caggtctggc gcgggacgat | 2460 |
| gcggggctcg gcgacggcgg cggtcatgga ccttgtttaa cccaggccgg cgtcggacgc | 2520 |
| atccgggcgg cttgcccgcc acgcccgccc gtgccacctg tcgcggatgc aggccgccgc | 2580 |
| ccccgacagt tccgcgccgg acctttttgct gctggggggc ggcctggcca acggccttct | 2640 |
| ggccctgcgc ctgtcccagg tccggcccga actggacgtg cggatcgtgg aggcggccga | 2700 |
| ccggctgggc gggatccata cctggtcctt cttcgaggcc gatctgacgc cggcgcagcg | 2760 |
| ggcgtggatc gcgcccctga tcgcctgtcg ctggcccggc tattccgtgc ggtttccggc | 2820 |
| gttcgaacgg cggttggtca ccggctattg cagcgtgacg gccgaacggt tcgccgaggc | 2880 |
| ggtgacccag gccctggcgg ggcgcatcgt caccggcgcc gccgtcgtct cggccgggcc | 2940 |
| gaccgaggcg gtcctggcgg acgggcaccg gctgacggcc cgggcggtca tcgacggccg | 3000 |
| ggggccgacc gctgcgccgg acctggccct ggggtttcag aaattcgtcg gcctggaggt | 3060 |
| gcggctgacc gcgcctcacg ggctgaagga accgatcgtc atggacgcct gcgtcgatca | 3120 |
| gtcagggggc tatcgcttcc tctatgtcct gcccttcgac gaccggaccc tgctgatcga | 3180 |
| ggacacccgc tacaccgacg gcgacgacct ggatcacgac ctgttccgaa cgggcgtcag | 3240 |
| ggactacgcc gcgcagcggg gctgggtcat agagacggtt ctgcgcgagg aggaggggt | 3300 |
| gctgccggtc gccctggacg gcgacatcgc cgcccatctg aagcggctgg ggccgacggc | 3360 |
| gctgagcggc ctgcgcgccg gtctgtttca tccgactacc ggctattccc tgccggacgc | 3420 |
| ggtgcggctg gcggatcatc tggcggagcg tatcgaagcg gcgccggacg gcccggccct | 3480 |
| ggcccaggtc atccgtcgcc atgcgcgcga cgtatgggcg caaagaggct tttatcggct | 3540 |

```
gctgaaccgc atgctgtttc gggccgcgcg gccggatcag aggtacaggg tgctggagcg    3600
gttctatcgc ctgcctcagc cgctgatcga acgcttctat gcgggggaga cgaccttggc    3660
cgacaaggcg cggatcctca gcggcaaacc cccggtgccg atcggcgccg ccctgacctg    3720
tctggtcgaa agaggacgtg cgtgatgcga gcagcagtga tcggatcggg gttcgggggg    3780
ctgtcgctgg ccattcgcct tcagacggcg gggatccaga ccacggtctt cgaggcgcgc    3840
gacctgccgg gcggccgggc ctatgtctat aaggacaagg gctataacctt cgacgccggg   3900
ccgaccgtca tcaccgatcc ttcggcgctg gaggagctgt cgagggcgc ggggcgcaag     3960
ctgtcggact atgtcgaact gctgccggtc gcccccttct atcggctgtg ctgggaagac    4020
ggcgacgtct tcgactacgt caacggccag gacgagctgg accgcagat cgtcgcccgc     4080
aacccggccg acaaggaggg ctatcgccgg ttcctggcct attcccagga cctgctgaag    4140
gaaggctatc tgaagctggg cgccgtgccc tttctggact cgccagcat ggtcaaggcg     4200
gcgccggagt tgatgcggct ccaggcctgg cgtcggtct atgacaaggt cgccggctat     4260
atccaggacg agcatctgcg tcaggccttc agctttcact ccctgctggt gggcggcaat    4320
ccgttcgcca cctcatcgat ctacgccctg atccacgcgc tggagcggcg ctggggcgtc    4380
tggttcccgc gcggcggcac cggcgccctg atccaggcca tggtgcggct gtttcaggac    4440
ctgggcggcg aaatccggct gaacagtccg gtcgagcgga tcaccctggc gaacgggcgc    4500
gccgacgggg tggtggtcgg cggccaggcc ctggccttcg acatggtcgc ctccaatgcg    4560
gacgtggtcc acacctatca gcgcctgctg gccaggagc cgcgcggccg caaggagggg     4620
gcgcgtctgg cctccaagcg gcattccatg tccttgttcg tcatctattt cggcctgaag    4680
cgggtccacc cggaggtgcg ccaccacacg gtgcttttcg gcccgcgcta ccgcgagctg    4740
atcggcgaaa tcttcaaggg gccggacctg ccccaggact tttccctcta tctgcacgcc    4800
ccgacccgca ccgatccgtc cctggcgccc gagggatgcg acgccttcta tgtgctggcg    4860
ccggtgccgc acctggcctc ggccgacatc gactgggcgg tcgaggggcc gcgctatcgc    4920
gacccgggtcc tggcctatct ggagcagcac tacattcccg gcctgacggc ccatctggac    4980
acctgccgca tcttcacgcc cgtggatttc cgcgaccagc tgaacgccca ccagggctcg    5040
gccttctcgc tggagccgat cctgacccag agcgcctatt ccgcgtcca taatcgcgac    5100
gaccagatcc ccaacctcta tttcgtcggc gccggcaccc atccgggcgc gggcgtgccg    5160
ggggtggtgg gctcggccaa ggccaccgcc ggcttgatga tcgaagatgc ggggcggacc    5220
gcatgagcga cgccgtcctg gaccacagcc gccagtcgat ggagcagggc tccaagagct    5280
tgcggccgc cgcccggctg tttcggcgg ccattcggga cgacgcctgg atgttctacg      5340
cctggtgccg ccattgcgac gacgagatcg acggccaggt cctgggccat ggggcggtcg    5400
gcatcgaccc ggtcctggcg gggcgcaaac tggtcgaact gcgcgaacgc acggccgccg    5460
ccctggccgg agagccgcag acggacccgg tcttcaccgc ctttcagcgc gtcgccgccc    5520
gccacgccat tccggcagag gaggcgatgg acctgttgca ggggttcgag atggacgtgg    5580
agggccgccg ctacgacacc ctggaggaca cgctggacta cgcctatcac gtcgccggcg    5640
tggtcggggt gatgatggcc cggatcatgg gggttcagga cgcgccgacc ctgccgccgcg   5700
cccaggacct gggcctggcc tttcagctga ccaacatcgc ccgagacgtg gtggaggacg    5760
ccaagggcgg gcgggtttat ctgcccggcc agtggctgga cgaggcgggc gtgccgcgcg    5820
accaggtcga tcagcccggg catcgtcagg ccgtcgccca tacggcccag cggctggtgg    5880
```

-continued

```
cggcggcgga gccctattac gcctcggcgc gctggggctt gcgcgatctc aatccgcgct    5940
cggcctgggc cgtcgccacg gcgcggggcg tctatcgcgc catcgccgc cacgtctcgc     6000
gctcgggcgc cacggcctgg gacggccgga cctcggtcga caaggcgggc aagctggccc    6060
tggtggggcg cggggccctg atcaccctgt ggtgcaagac cctggacgcc tggcgtgaac    6120
cgccgccgcg cccggccctg tggacccaca tctgacggcg ctcagcgccc ggcgcgtctg    6180
tgctccatca tcacggccag ggcgatcccg gccagaccca cgccgccag gcgcgccag     6240
ccggccagga ccccgcgtt gaagtcgccg cgccagatca gggcctgata ggtctccacg     6300
gcccaggcat ggggcgtgat ccagcccagg gcgcggaagg cttcgggcat caggaagcgc    6360
ggcgccatcg acccgcccag ggccgccagc agcagggcga cgaaggtggt caggggctgg    6420
gcctgttcgc gcgaccgaca ggccgccgtc agggccaggg ccaccccgcc gcgcacagg    6480
gcgaccaggg cggcggtcag gagcgccgcc gccgcctgcc aaaacgcaag atccggcagc    6540
cgaggccagg ccgccaggaa gacggccgcc gactgcatca ggccgaccgt cgtcagccag    6600
atcgcccgtc ccgccagtat gggcgccgtc ccgcccgcg ccagggccag ccgcgcctgc    6660
aggcccgagc gccgttcgtc caacccgccc atggcgccgt gcatggcggc gaagaagacg    6720
aacatcacgc tgaccgcccc ggcgtaatag gcggcctgga cgtcgccctg cggccccacc    6780
tggcggacgg ggacgtcgcg cgacggggc gcgggccgac cggccagggc cgccgccgca    6840
gggaccagcc gcgcctgaag cgccgccgcc gccacgtctc gacccgccgc cgacaccacc    6900
gtcagctggg gcgcgcctgc atcgtcgcgg gtgatcagaa cgccggcgtc ggcgcggccg    6960
tcgatcacgg cccgctccac cgcctgggcg tcgtccagac ggcgaaggcg cggccccaga    7020
tcccgcgaca gcgcctcgcc gacggcggcc cggccggg tgcgcgccgc atcgtgcagg    7080
gccacgctgg cgtcgatgtc gccacgcgcc ccggcgccga agacggcggc gaacagcaga    7140
tagaccaggg gcggcaaaac cagggtcagg gccatgcccg aacggtcccg ccagaagccg    7200
cgcgcccagg cgcccgccac cgccatcatg acgaggcgtc cgacagatgg gcgaccaggt    7260
cgtccaggcc ggggcgacgc acggcgacct cgcccccctc ggcgtccgcc tcgggcgaaa    7320
ccctctgggc cgcgcccagg gcgtcctcgc acagcagccg ccattccagc ccgtccttgg    7380
agggcgccag acccgactgg gcgaaccggc tcgcggccag gcgcgaggcg ggccgcggca    7440
gtttgacgac cagcagccgc gccaggccga aggcctgacg cagcagggcc ttgggcggtc    7500
cttccgccag cagccggccc tgggccagga cgccgatccg atcggccgtc tcggagacga    7560
aggcctcgtc gtggctgatc agcagacagc cggcgcccgc ctggaccgtc tcgcgcaggg    7620
cggacgacag gacgacgcgg gcggcggcgt ccacccttc ggtcggttcg tcggcgatca    7680
gcaggcgcgc gcgcccgacc agggcggcgc tgaggttggc gcgccgacgc catccgcccg    7740
acagtgaatg aaccggctcg tccgccctgg gggcgcatcc ggtcagggcc agggcccgct    7800
ccaccgccgc agggcggttg aacgggaa ggccgcacag ggccgcgacc ccgcgacgt     7860
tctcgcgcgg cgtcagggcg ggaaagaggg cgcagtcctg gggcgcaagg ccgatgcgtc    7920
cgcgacgggg cgcgccttcg ccggccgtcg cccgcccgcg ccggacgggg atcaggccgc    7980
aggccacccg agccgccgtg gacttgcccg ccccgttcgg acccagcagg gcgtaaacct    8040
ctccggccgc gacggtcagg ttgaaatcgc gcagcaccgg cccttcgccg tagcccgcct    8100
cgacgtcctt cagaaccagc gccggcgcga cgctagcgtc caagttcggc ctgccggaag    8160
agatgaagga cataggtcgt caggggggctg tcgtgcccga ccgcctcggc cgcccgggcc    8220
agtgactggc gcaccccggc gcggacccgg ccttcgcccc acaggtccac gaaggtggtc    8280
```

```
acgccctgat cctgacccac gtccttgccc aaggcctcgc tcgtcgaaca ggcgtccatc    8340
aggtcgtcgc aaagctggaa ggcgaagccg accgcttcgc cgaaggcggc gagacgcgcc    8400
aggtcgtccg catcgccgcc gcccatccgg ccgccgcccc gcgcggccgc gacgaacagg    8460
gcgccggtct tcagatcgtt gatccgacgc agggcgacca cgtcgcgctg aacgggatcg    8520
tcgcgcagat cgcgcatctg gccctcggcc aggccgtcga agccgatcgc ctgcgtcaaa    8580
tcgtccaggg cgcccagccg cgcctccgac ggcgcccggc tttgcagaat cagccgggtc    8640
gattggttca aaagggccac ggccgccagc acggccgcat cctcgccgtg gcggcggtgc    8700
agggtcggct gaccgcgccg caaggccgca tcatccatac agggcaggtc gtccagaacc    8760
agggaggcgg catgggccat tcgaccgcg caaccgaaat ccaggcgtc ctcggcccgc      8820 ccgccgacgt gcgcggcggc caacatggcc acgaccggcc tgacccgctt gcccggtccc    8880
agcagggcct cgcgcgcggc gagggctaaa agaccgtccg atgagggcgc cgtctcggcc    8940
agccggtcct gcaccaggcc acgcagattc tcgggcgact gaggttcggg gtccgacacg    9000
ggctggggcc ttaagccgac gatcgccata cgggtctcct gatgtccttc gacagtcgcg    9060
ttgcgaccct gggctgacgc attatgatca catacggcat cacgactgcg tcggatgcaa    9120
cccgccagag catgatcgtt tcggagggaa ccgctaggag cgtttgcgat gcccaccccc    9180
gacgacgccc tgatccgacg caaggacgaa cacatcgacc acgtgcgggc cggacggggt    9240
ctcagcggcg cgtcctcggg actggaggcg gtgcgtttcg tccatgacgc cttgccggac    9300
ctggccctcg accagatcga cctgtccgcc cgttttcctgg gcggcggct gaacctgccc     9360 ttcctgatca gttcgatgac cggcggcccg tcgcgggccg aggcgatcaa tgcgcggctg    9420
gccgaggcgg cccaggccct gggcgtggcc ctggcggtcg gctcccagcg cgtcgccctg    9480
gagacggccg gcgggtccgg cggctcgggc ttggggccgg atctgcgccg ccgggcgccc    9540
gacgccctga tcctggccaa tctggggcg gtgcagttcg ccctgggcta tggggtggac     9600
gaggcgcgcc gggccatgga gatgatcggc gccgacgccc tgatcctgca tctgaatccg    9660
cttcaggaag gcgtccagcc cgagggcgac cgcgactggc gcggcgtggc ccagggatc     9720 gagcggatcg ccgccgcctt tccgggccag gtggtggtca aggagaccgg cgccggcctg    9780
tcggccgccg tcgcccggcg cctggccgac atgggcgtcg cggccctgga cgtggcgggg    9840
gcgggcggca ccaactgggg cctgatcgaa ggggcgcggg ccaccggcgg gcgggccgag    9900
gccttggccg ccccccttcg cgactggggg gtgccgacgg cccgcagcct ccgcgactgc    9960
gcccaggccg cccccggacct ggggctgatc ggctcgggcg ggatcaagga cggtctggat   10020
gcggcccgcg ccgtccgcct gggggccgat ctggtcggcc aggccgccgg ggtgctggag   10080
gcggccctga cctcgaccca gcggtggtc gatcatttcg agctgatggc ggcccagctg     10140
cggctcgcct gtttctgcac gggctccgcc gatctggcgg ccctcgctca ggcgccgctg   10200
ctggaagagc cccgcttctg agccagttcg gccttcagcg cccgcgccga ccgcacccac    10260
agaaagccga aggagacgca gccttcgcgc gtgcgcacgg cgtgatgcag acggtgcgcc    10320
tggatgcgcc gcgtccagaa gccggaccgc ccggaaaagc ccgtcgggaa ccgccggtgc    10380
accaggccgt cgtggaagaa gaaatagacc atcccatagg ccgtgatccc caggccgacc    10440
ggcagggccc agggccacag gtgcagaccc acggccacca tgacgatggc cggggcggcg    10500
aagaccacgg cgaacaggtc gttcttctcc agggggtgat cgtgcggctc atgatggctg    10560
cggtgccagg accacaggaa accgtgcatc acatagcggt gcatgatcca ggcgaacgcc    10620
```

-continued

```
tccatgccca aaaaggcggt caggaacagc gcgatccacg tcagccaggc catggcccca      10680
gcataggcgg tttgatccgc cttcgccacg acttgaccgc cgcagggatt tgaccgtctg      10740 tgccccc atg ttg agg gat ctg ctc atc acc acc ctg gcg ctg agc ctg        10789
        Met Leu Arg Asp Leu Leu Ile Thr Thr Leu Ala Leu Ser Leu
        1               5                   10 atc atc ggc ctg cgc tat ctg ctg gtc ggc gcg gcc cat ggg ctg            10837
Ile Ile Gly Leu Arg Tyr Leu Leu Val Gly Ala Ala His Gly Leu
15              20                  25                  30 ctg tgg gcc ggg gcg ggc cgg gga cgg gcg ctg aac ctg cgg ccg ccg        10885
Leu Trp Ala Gly Ala Gly Arg Gly Arg Ala Leu Asn Leu Arg Pro Pro
        35                  40                  45 gcg atg aag cgc atc cgc gcc gag atc gtc gcc tcc ctg atc gcc tgc        10933
Ala Met Lys Arg Ile Arg Ala Glu Ile Val Ala Ser Leu Ile Ala Cys
        50                  55                  60 ccc atc tac gcc ctg ccg gcg gcc ctg gtg ctg gag ctg tgg aag cgg        10981
Pro Ile Tyr Ala Leu Pro Ala Ala Leu Val Leu Glu Leu Trp Lys Arg
        65                  70                  75 ggc ggg acg gcg atc tac agc gat ccc gac gcc tgg ccc ctg tgg tgg        11029
Gly Gly Thr Ala Ile Tyr Ser Asp Pro Asp Ala Trp Pro Leu Trp Trp
80                  85                  90 ctg ccg gtc agt ctg atc gtc tat ctg ctg gcg cac gac gcc ttc tac        11077
Leu Pro Val Ser Leu Ile Val Tyr Leu Leu Ala His Asp Ala Phe Tyr
95                  100                 105                 110 tac tgg gtg cac agg gcc ctg cat cac ccg cgc gtc ttc ggc tgg gcc        11125
Tyr Trp Val His Arg Ala Leu His His Pro Arg Val Phe Gly Trp Ala
            115                 120                 125 cat gcc gaa cac cac cgg tcg cgc gac ccc agc gcc ttc gcc tcc ttc        11173
His Ala Glu His His Arg Ser Arg Asp Pro Ser Ala Phe Ala Ser Phe
            130                 135                 140 gcc ttc gac ccg gcc gag gct gcg gcc acc gcc tgg ttc ctg ccc gcc        11221
Ala Phe Asp Pro Ala Glu Ala Ala Ala Thr Ala Trp Phe Leu Pro Ala
        145                 150                 155 ctg gcc ctg atc gtg ccg atc cac tgg ggc gtg gcc ctg acc ctg ctg        11269
Leu Ala Leu Ile Val Pro Ile His Trp Gly Val Ala Leu Thr Leu Leu
        160                 165                 170 acg ctg atg tcg ctg acg gcc gcc ctg aac cat gcg ggg cgc gag gtc        11317
Thr Leu Met Ser Leu Thr Ala Ala Leu Asn His Ala Gly Arg Glu Val
175                 180                 185                 190 tgg ccc gcc gcc tgg ctg gag cgg gcg ccg ctt cgc tgg ctg atc acc        11365
Trp Pro Ala Ala Trp Leu Glu Arg Ala Pro Leu Arg Trp Leu Ile Thr
            195                 200                 205 gcc acc cac cac gac gcc cac cac aag cgg ttc aac gga aac tac ggc        11413
Ala Thr His His Asp Ala His His Lys Arg Phe Asn Gly Asn Tyr Gly
            210                 215                 220 ctc tat ttc cag ttc tgg gac cgc tgg gcc ggg act gag gtt tcg gcc        11461
Leu Tyr Phe Gln Phe Trp Asp Arg Trp Ala Gly Thr Glu Val Ser Ala
        225                 230                 235 gcc ccc tcg cca cca tcc ccg gtc atc cct cca gag cgg ccc tca gcg        11509
Ala Pro Ser Pro Pro Ser Pro Val Ile Pro Pro Glu Arg Pro Ser Ala
        240                 245                 250 cct ctt cgg tgatcggctt ggtcagggcg ggcgtgggcg cccaggccgg                11558
Pro Leu Arg
255 tcgccatctg cagtatggac gacgaggcca gacgtccccc gccgctcatg gcgatgaccc      11618 gcagggagtc cctcaaatgc cgggtgtcca tgatgaagtt cagcccgtcg cggtccggca      11678 tcagaatgtc caccagcacg gcgtcgggcg accagtcctc gacgatccgc aaccgtcgt       11738 tgaccgttgc tgcggtcagg acttggcaac ccagccgttt cagcatctcc tccagatgaa     11798
```

```
gcagaaccag cgaatcgtcc tcgatcacgc agactttcac gcccaacctc cagatgcgat    11858 caggggaac taacggatga atcccatgtt gcgtcaactc ggaagacggc gtttccgact     11918
ggccatcgcc ttggcgggcg cggtcgtgac cctgcttctg cggccactg gggtgacgct     11978 gcaacgagaa ttc                                                       11991

<210> SEQ ID NO 3
<211> LENGTH: 774
<212> TYPE: DNA
<213> ORGANISM: Brevundimonas sp.
<220> FEATURE:
<221> NAME/KEY: CDS
<222> LOCATION: (1)..(771)

<400> SEQUENCE: 3 atg ttg agg gat ctg ctc atc acc acc ctg gcg ctg agc ctg atc atc       48
Met Leu Arg Asp Leu Leu Ile Thr Thr Leu Ala Leu Ser Leu Ile Ile
 1               5                  10                  15 ggc ctg cgc tat ctg ctg gtc ggc gcg gcg gcc cat ggg ctg ctg tgg       96
Gly Leu Arg Tyr Leu Leu Val Gly Ala Ala Ala His Gly Leu Leu Trp
             20                  25                  30 gcc ggg gcg ggc cgg gga cgg gcg ctg aac ctg cgg ccg ccg gcg atg      144
Ala Gly Ala Gly Arg Gly Arg Ala Leu Asn Leu Arg Pro Pro Ala Met
         35                  40                  45 aag cgc atc cgc gcc gag atc gtc gcc tcc ctg atc gcc tgc ccc atc      192
Lys Arg Ile Arg Ala Glu Ile Val Ala Ser Leu Ile Ala Cys Pro Ile
     50                  55                  60 tac gcc ctg ccg gcg gcc ctg gtg ctg gag ctg tgg aag cgg ggc ggg      240
Tyr Ala Leu Pro Ala Ala Leu Val Leu Glu Leu Trp Lys Arg Gly Gly
 65                  70                  75                  80 acg gcg atc tac agc gat ccc gac gcc tgg ccc ctg tgg tgg ctg ccg      288
Thr Ala Ile Tyr Ser Asp Pro Asp Ala Trp Pro Leu Trp Trp Leu Pro
                 85                  90                  95 gtc agt ctg atc gtc tat ctg ctg gcg cac gac gcc ttc tac tac tgg      336
Val Ser Leu Ile Val Tyr Leu Leu Ala His Asp Ala Phe Tyr Tyr Trp
            100                 105                 110 gtg cac agg gcc ctg cat cac ccg cgc gtc ttc ggc tgg gcc cat gcc      384
Val His Arg Ala Leu His His Pro Arg Val Phe Gly Trp Ala His Ala
        115                 120                 125 gaa cac cac cgg tcg cgc gac ccc agc gcc ttc gcc tcc ttc gcc ttc      432
Glu His His Arg Ser Arg Asp Pro Ser Ala Phe Ala Ser Phe Ala Phe
    130                 135                 140 gac ccg gcc gag gct gcg gcc acc gcc tgg ttc ctg ccc gcc ctg gcc      480
Asp Pro Ala Glu Ala Ala Ala Thr Ala Trp Phe Leu Pro Ala Leu Ala
145                 150                 155                 160 ctg atc gtg ccg atc cac tgg ggc gtg gcc ctg acc ctg acg ctg           528
Leu Ile Val Pro Ile His Trp Gly Val Ala Leu Thr Leu Thr Leu
                165                 170                 175 atg tcg ctg acg gcc gcc ctg aac cat gcg ggg cgc gag gtc tgg ccc      576
Met Ser Leu Thr Ala Ala Leu Asn His Ala Gly Arg Glu Val Trp Pro
            180                 185                 190 gcc gcc tgg ctg gag cgg gcg ccg ctt cgc tgg ctg atc acc gcc acc      624
Ala Ala Trp Leu Glu Arg Ala Pro Leu Arg Trp Leu Ile Thr Ala Thr
        195                 200                 205 cac cac gac gcc cac cac aag cgg ttc aac gga aac tac ggc ctc tat      672
His His Asp Ala His His Lys Arg Phe Asn Gly Asn Tyr Gly Leu Tyr
    210                 215                 220 ttc cag ttc tgg gac cgc tgg gcc ggg act gag gtt tcg gcc gcc ccc      720
Phe Gln Phe Trp Asp Arg Trp Ala Gly Thr Glu Val Ser Ala Ala Pro
225                 230                 235                 240
```

```
tcg cca cca tcc ccg gtc atc cct cca gag cgg ccc tca gcg cct ctt    768
Ser Pro Pro Ser Pro Val Ile Pro Pro Glu Arg Pro Ser Ala Pro Leu
                245                 250                 255 cgg tga                                                             774
Arg
```

<210> SEQ ID NO 4
<211> LENGTH: 257
<212> TYPE: PRT
<213> ORGANISM: Brevundimonas sp.

<400> SEQUENCE: 4

```
Met Leu Arg Asp Leu Leu Ile Thr Thr Leu Ala Leu Ser Leu Ile Ile
  1               5                  10                  15

Gly Leu Arg Tyr Leu Leu Val Gly Ala Ala His Gly Leu Leu Trp
             20                  25                  30

Ala Gly Ala Gly Arg Gly Arg Ala Leu Asn Leu Arg Pro Pro Ala Met
         35                  40                  45

Lys Arg Ile Arg Ala Glu Ile Val Ala Ser Leu Ile Ala Cys Pro Ile
 50                  55                  60

Tyr Ala Leu Pro Ala Ala Leu Val Leu Glu Leu Trp Lys Arg Gly Gly
 65                  70                  75                  80

Thr Ala Ile Tyr Ser Asp Pro Asp Ala Trp Pro Leu Trp Trp Leu Pro
                 85                  90                  95

Val Ser Leu Ile Val Tyr Leu Leu Ala His Asp Ala Phe Tyr Tyr Trp
            100                 105                 110

Val His Arg Ala Leu His His Pro Arg Val Phe Gly Trp Ala His Ala
        115                 120                 125

Glu His His Arg Ser Arg Asp Pro Ser Ala Phe Ala Ser Phe Ala Phe
    130                 135                 140

Asp Pro Ala Glu Ala Ala Ala Thr Ala Trp Phe Leu Pro Ala Leu Ala
145                 150                 155                 160

Leu Ile Val Pro Ile His Trp Gly Val Ala Leu Thr Leu Leu Thr Leu
                165                 170                 175

Met Ser Leu Thr Ala Ala Leu Asn His Ala Gly Arg Glu Val Trp Pro
            180                 185                 190

Ala Ala Trp Leu Glu Arg Ala Pro Leu Arg Trp Leu Ile Thr Ala Thr
        195                 200                 205

His His Asp Ala His His Lys Arg Phe Asn Gly Asn Tyr Gly Leu Tyr
    210                 215                 220

Phe Gln Phe Trp Asp Arg Trp Ala Gly Thr Glu Val Ser Ala Ala Pro
225                 230                 235                 240

Ser Pro Pro Ser Pro Val Ile Pro Pro Glu Arg Pro Ser Ala Pro Leu
                245                 250                 255

Arg
```

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tacgaattcg atgcccctcg ccctg                                         25

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tagaggatcc tcaaggagtg aactggatcg ta                                    32

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tacgaattcg atgaccgccg ccgtcg                                           26

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagaggatcc tcaagactcg ccgcgccaca a                                     31

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tacgaattcg ctgtcgcgga tgcaggc                                          27

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tagaggatcc tgcggttcag cagccgataa aa                                    32

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tacgaattcg atgcgagcag cagtgatcgg a                                     31

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 12
tagaggatcc aagctcttgg agccctgct                                    29

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tacgaattcg atgagcgacg ccgtcct                                      27

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tagaggatcc tcagatgtgg gtccacagg                                    29

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tacgaattcg atgatggcgg tggcgggc                                     28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tagaggatcc cccacatctg acggcgct                                     28

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tacgaattcg atgtccttca tctcttccgg c                                 31

<210> SEQ ID NO 18
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagaggatcc accgccatca tgacgagg                                          28

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tacgaattcg atggcgatcg tcggcttaa                                         29

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tagaggatcc ctagcgtcca agttcggcct                                        30

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tacgaattcg atgcccaccc ccgacgacg                                         29

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tagaggatcc tcagaagcgg ggctcttcca                                        30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tacgaattcg atggcctggc tgacgtggat                                        30

<210> SEQ ID NO 24
<211> LENGTH: 29
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 24
tagaggatcc tcaggcgccg ctgctggaa                                    29

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tacgaattcg atgttgaggg atctgctcat ca                                32

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tagaggatcc tcaccgaaga ggcgctgag                                    29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tacgaattcg atgctgaaac ggctgggtt                                    29

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tagaggatcc ctatttccag ttctgggacc g                                 31

<210> SEQ ID NO 29
<211> LENGTH: 486
<212> TYPE: DNA
<213> ORGANISM: Brevundimonas sp.
<220> FEATURE:
<221> NAME/KEY: CDS
<222> LOCATION: (1)..(483)

<400> SEQUENCE: 29 atg gcc tgg ctg acg tgg atc gcg ctg ttc ctg acc gcc ttt ttg ggc     48
Met Ala Trp Leu Thr Trp Ile Ala Leu Phe Leu Thr Ala Phe Leu Gly
 1               5                  10                  15 atg gag gcg ttc gcc tgg atc atg cac cgc tat gtg atg cac ggt ttc     96
Met Glu Ala Phe Ala Trp Ile Met His Arg Tyr Val Met His Gly Phe
             20                  25                  30

```
ctg tgg tcc tgg cac cgc agc cat cat gag ccg cac gat cac ccc ctg    144
Leu Trp Ser Trp His Arg Ser His His Glu Pro His Asp His Pro Leu
         35                  40                  45 gag aag aac gac ctg ttc gcc gtg gtc ttc gcc gcc ccg gcc atc gtc    192
Glu Lys Asn Asp Leu Phe Ala Val Val Phe Ala Ala Pro Ala Ile Val
 50                  55                  60 atg gtg gcc gtg ggt ctg cac ctg tgg ccc tgg gcc ctg ccg gtc ggc    240
Met Val Ala Val Gly Leu His Leu Trp Pro Trp Ala Leu Pro Val Gly
 65                  70                  75                  80 ctg ggg atc acg gcc tat ggg atg gtc tat ttc ttc ttc cac gac ggc    288
Leu Gly Ile Thr Ala Tyr Gly Met Val Tyr Phe Phe Phe His Asp Gly
                 85                  90                  95 ctg gtg cac cgg cgg ttc ccg acg ggc ttt tcc ggg cgg tcc ggc ttc    336
Leu Val His Arg Arg Phe Pro Thr Gly Phe Ser Gly Arg Ser Gly Phe
            100                 105                 110 tgg acg cgg cgc atc cag gcg cac cgt ctg cat cac gcc gtg cgc acg    384
Trp Thr Arg Arg Ile Gln Ala His Arg Leu His His Ala Val Arg Thr
        115                 120                 125 cgc gaa ggc tgc gtc tcc ttc ggc ttt ctg tgg gtg cgg tcg gcg cgg    432
Arg Glu Gly Cys Val Ser Phe Gly Phe Leu Trp Val Arg Ser Ala Arg
130                 135                 140 gcg ctg aag gcc gaa ctg gct cag aag cgg ggc tct tcc agc agc ggc    480
Ala Leu Lys Ala Glu Leu Ala Gln Lys Arg Gly Ser Ser Ser Ser Gly
145                 150                 155                 160 gcc tga                                                            486
Ala
```

<210> SEQ ID NO 30
<211> LENGTH: 161
<212> TYPE: PRT
<213> ORGANISM: Brevundimonas sp.

<400> SEQUENCE: 30

```
Met Ala Trp Leu Thr Trp Ile Ala Leu Phe Leu Thr Ala Phe Leu Gly
  1               5                  10                  15

Met Glu Ala Phe Ala Trp Ile Met His Arg Tyr Val Met His Gly Phe
                 20                  25                  30

Leu Trp Ser Trp His Arg Ser His His Glu Pro His Asp His Pro Leu
             35                  40                  45

Glu Lys Asn Asp Leu Phe Ala Val Val Phe Ala Ala Pro Ala Ile Val
 50                  55                  60

Met Val Ala Val Gly Leu His Leu Trp Pro Trp Ala Leu Pro Val Gly
 65                  70                  75                  80

Leu Gly Ile Thr Ala Tyr Gly Met Val Tyr Phe Phe Phe His Asp Gly
                 85                  90                  95

Leu Val His Arg Arg Phe Pro Thr Gly Phe Ser Gly Arg Ser Gly Phe
            100                 105                 110

Trp Thr Arg Arg Ile Gln Ala His Arg Leu His His Ala Val Arg Thr
        115                 120                 125

Arg Glu Gly Cys Val Ser Phe Gly Phe Leu Trp Val Arg Ser Ala Arg
130                 135                 140

Ala Leu Lys Ala Glu Leu Ala Gln Lys Arg Gly Ser Ser Ser Ser Gly
145                 150                 155                 160

Ala
```

<210> SEQ ID NO 31
<211> LENGTH: 897

<212> TYPE: DNA
<213> ORGANISM: Brevundimonas sp.
<220> FEATURE:
<221> NAME/KEY: CDS
<222> LOCATION: (1)..(894)

<400> SEQUENCE: 31

```
atg gcg atc gtc ggc tta agg ccc cag ccc gtg tcg gac ccc gaa cct      48
Met Ala Ile Val Gly Leu Arg Pro Gln Pro Val Ser Asp Pro Glu Pro
 1               5                  10                  15 cag tcg ccc gag aat ctg cgt ggc ctg gtg cag gac cgg ctg gcc gag      96
Gln Ser Pro Glu Asn Leu Arg Gly Leu Val Gln Asp Arg Leu Ala Glu
             20                  25                  30 acg gcg ccc tca tcg gac ggt ctt tta gcc ctc gcc gcg cgc gag gcc     144
Thr Ala Pro Ser Ser Asp Gly Leu Leu Ala Leu Ala Ala Arg Glu Ala
         35                  40                  45 ctg ctg gga ccg ggc aag cgg gtc agg ccg gtc gtg gcc atg ttg gcc     192
Leu Leu Gly Pro Gly Lys Arg Val Arg Pro Val Val Ala Met Leu Ala
     50                  55                  60 gcc gcg cac gtc ggc ggg cgg gcc gag gac gcc ctg gat ttc ggt tgc     240
Ala Ala His Val Gly Gly Arg Ala Glu Asp Ala Leu Asp Phe Gly Cys
 65                  70                  75                  80 gcg gtc gaa atg gcc cat gcc gcc tcc ctg gtt ctg gac gac ctg ccc     288
Ala Val Glu Met Ala His Ala Ala Ser Leu Val Leu Asp Asp Leu Pro
                 85                  90                  95 tgt atg gat gat gcg gcc ttg cgg cgc ggt cag ccg acc ctg cac cgc     336
Cys Met Asp Asp Ala Ala Leu Arg Arg Gly Gln Pro Thr Leu His Arg
            100                 105                 110 cgc cac ggc gag gat gcg gcc gtg ctg gcg gcc gtg gcc ctt ttg aac     384
Arg His Gly Glu Asp Ala Ala Val Leu Ala Ala Val Ala Leu Leu Asn
        115                 120                 125 caa tcg acc cgg ctg att ctg caa agc cgg gcg ccg tcg gag gcg cgg     432
Gln Ser Thr Arg Leu Ile Leu Gln Ser Arg Ala Pro Ser Glu Ala Arg
    130                 135                 140 ctg ggc gcc ctg gac gat ttg acg cag gcg atc ggc ttc gac ggc ctg     480
Leu Gly Ala Leu Asp Asp Leu Thr Gln Ala Ile Gly Phe Asp Gly Leu
145                 150                 155                 160 gcc gag ggc cag atg cgc gat ctg cgc gac gat ccc gtt cag cgc gac     528
Ala Glu Gly Gln Met Arg Asp Leu Arg Asp Asp Pro Val Gln Arg Asp
                165                 170                 175 gtg gtc gcc ctg cgt cgg atc aac gat ctg aag acc ggc gcc ctg ttc     576
Val Val Ala Leu Arg Arg Ile Asn Asp Leu Lys Thr Gly Ala Leu Phe
            180                 185                 190 gtc gcg gcc gcg cgg ggc ggc ggc cgg atg ggc ggc ggc gat gcg gac     624
Val Ala Ala Ala Arg Gly Gly Gly Arg Met Gly Gly Gly Asp Ala Asp
        195                 200                 205 gac ctg gcg cgt ctc gcc gcc ttc ggc gaa gcg gtc ggc ttc gcc ttc     672
Asp Leu Ala Arg Leu Ala Ala Phe Gly Glu Ala Val Gly Phe Ala Phe
    210                 215                 220 cag ctt tgc gac gac ctg atg gac gcc tgt tcg acg agc gag gcc ttg     720
Gln Leu Cys Asp Asp Leu Met Asp Ala Cys Ser Thr Ser Glu Ala Leu
225                 230                 235                 240 ggc aag gac gtg ggt cag gat cag ggc gtg acc acc ttc gtg gac ctg     768
Gly Lys Asp Val Gly Gln Asp Gln Gly Val Thr Thr Phe Val Asp Leu
                245                 250                 255 tgg ggc gaa ggc cgg gtc cgc gcc ggg gtg cgc cag tca ctg gcc cgg     816
Trp Gly Glu Gly Arg Val Arg Ala Gly Val Arg Gln Ser Leu Ala Arg
            260                 265                 270 gcg gcc gag gcg gtc ggg cac gac agc ccc ctg acg acc tat gtc ctt     864
Ala Ala Glu Ala Val Gly His Asp Ser Pro Leu Thr Thr Tyr Val Leu
        275                 280                 285
```

```
cat ctc ttc cgg cag gcc gaa ctt gga cgc tag                                    897
His Leu Phe Arg Gln Ala Glu Leu Gly Arg
    290                 295
```

<210> SEQ ID NO 32
<211> LENGTH: 298
<212> TYPE: PRT
<213> ORGANISM: Brevundimonas sp.

<400> SEQUENCE: 32

```
Met Ala Ile Val Gly Leu Arg Pro Gln Pro Val Ser Asp Pro Glu Pro
 1               5                  10                  15

Gln Ser Pro Glu Asn Leu Arg Gly Leu Val Gln Asp Arg Leu Ala Glu
            20                  25                  30

Thr Ala Pro Ser Ser Asp Gly Leu Leu Ala Leu Ala Ala Arg Glu Ala
        35                  40                  45

Leu Leu Gly Pro Gly Lys Arg Val Arg Pro Val Ala Met Leu Ala
    50                  55                  60

Ala Ala His Val Gly Gly Arg Ala Glu Asp Ala Leu Asp Phe Gly Cys
 65                  70                  75                  80

Ala Val Glu Met Ala His Ala Ala Ser Leu Val Leu Asp Asp Leu Pro
                85                  90                  95

Cys Met Asp Asp Ala Ala Leu Arg Arg Gly Gln Pro Thr Leu His Arg
            100                 105                 110

Arg His Gly Glu Asp Ala Ala Val Leu Ala Ala Val Ala Leu Leu Asn
        115                 120                 125

Gln Ser Thr Arg Leu Ile Leu Gln Ser Arg Ala Pro Ser Glu Ala Arg
    130                 135                 140

Leu Gly Ala Leu Asp Asp Leu Thr Gln Ala Ile Gly Phe Asp Gly Leu
145                 150                 155                 160

Ala Glu Gly Gln Met Arg Asp Leu Arg Asp Asp Pro Val Gln Arg Asp
                165                 170                 175

Val Val Ala Leu Arg Arg Ile Asn Asp Leu Lys Thr Gly Ala Leu Phe
            180                 185                 190

Val Ala Ala Ala Arg Gly Gly Gly Arg Met Gly Gly Gly Asp Ala Asp
        195                 200                 205

Asp Leu Ala Arg Leu Ala Ala Phe Gly Glu Ala Val Gly Phe Ala Phe
    210                 215                 220

Gln Leu Cys Asp Asp Leu Met Asp Ala Cys Ser Thr Ser Glu Ala Leu
225                 230                 235                 240

Gly Lys Asp Val Gly Gln Asp Gln Gly Val Thr Thr Phe Val Asp Leu
                245                 250                 255

Trp Gly Glu Gly Arg Val Arg Ala Gly Val Arg Gln Ser Leu Ala Arg
            260                 265                 270

Ala Ala Glu Ala Val Gly His Asp Ser Pro Leu Thr Thr Tyr Val Leu
        275                 280                 285

His Leu Phe Arg Gln Ala Glu Leu Gly Arg
    290                 295
```

<210> SEQ ID NO 33
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 33
gtcccgagaa ggaggctaga tatgtccgct cacgctttgc                              40

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cggcggccgc ccgggactaa gcggtgtcac ccttggttct                              40

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgcggccgc ttataaggac agcccgaatg                                        30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cagtcgacat ccttaactga cggcagcgag                                        30

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (9)..(9)
<223> OTHER INFORMATION: n is I
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (18)..(18)
<223> OTHER INFORMATION: n is I

<400> SEQUENCE: 37
ttygaygcng gnccnacngt                                                   20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
        primer
<220> FEATURE:
<221> NAME/KEY: misc_feature
<222> LOCATION: (3)..(3)
<223> OTHER INFORMATION: n is I
<220> FEATURE:
<221> NAME/KEY: misc_feature
<222> LOCATION: (9)..(9)
<223> OTHER INFORMATION: n is I
<220> FEATURE:
<221> NAME/KEY: misc_feature
<222> LOCATION: (12)..(12)
<223> OTHER INFORMATION: n is I
<220> FEATURE:
<221> NAME/KEY: misc_feature
<222> LOCATION: (15)..(15)
<223> OTHER INFORMATION: n is I
<220> FEATURE:
<221> NAME/KEY: misc_feature
<222> LOCATION: (18)..(18)
<223> OTHER INFORMATION: n is I

<400> SEQUENCE: 38
ccnggrtgng tnccngcncc                                           20
```

CAROTENOID HYDROXYLASE GENE, METHOD FOR PREPARING HYDROXYLATED CAROTENOID, AND NOVEL GERANYLGERANYL PYROPHOSPHATE SYNTHASE

TECHNICAL FIELD

The present invention relates to a novel enzyme that introduces a hydroxyl group at the position 2 (2') carbon of the β-ionone ring in carotenoids, a gene encoding the enzyme, and a microorganism into which the gene is introduced. The present invention also relates to a method of preparing a carotenoid in which the position 2 carbon of its β-ionone ring is hydroxylated, using the above microorganism.

Further, the present invention relates to a gene encoding a novel enzyme that introduces a hydroxyl group at the position 3 (3') carbon of the β-ionone ring in carotenoids, and a microorganism into which the gene is introduced. The present invention also relates to a method of preparing a carotenoid in which the position 3 carbon of its β-ionone ring is hydroxylated, using the above microorganism.

Further, the present invention relates to a gene encoding a novel geranylgeranyl pyrophosphate (GGPP) synthase.

BACKGROUND ART

Carotenoid (also called "carotinoid") is a general term for pigments occurring abundantly in nature, which are built up from an isoprene backbone of 40 carbon atoms. To date, more than 700 species of carotenoids have been isolated (Britton, G., Liaaen-Jensen, S., and Pfander, H., Carotenoids Handbook, Birkhauser Verlag, Basel, 2004). Recently, prophylactic effects of carotenoids on chronic diseases such as cancer have attracted people's attention, and a great number of reports have been made (see, for example, H. Nishino, M. Murakoshi and M. Yano, Food Style 21, 4, 53-55, 2000; Nishino, H. et al, "Carotenoids in cancer chemoprevention", Cancer Metastasis Rev. 21, 257-264, 2002; Mayne, S. T., "β-Carotene, carotenoids, and disease prevention in humans", FASEB J., 10, 690-701, 1996).

Although carotenoids have a huge variety of species, species which have been used in prophylactic studies (human epidemiological/clinical tests, animal administration tests, etc.) are extremely limited. Those carotenoids include β-carotene (also called β-carotine; chemically synthesized product), lycopene (also called lycopine; extracted from tomato), α-carotene (also called α-carotine; extracted from palm oil), lutein (extracted from marigold), astaxanthin (extracted from krill or *Haematococcus* alga, or chemically synthesized), fucoxanthin (extracted from edible marine algae) and β-cryptoxanthin (extracted from mandarin orange). The results of cancer prophylactic studies using these pigments gradually revealed that cancer prophylactic effects of carotenoids vary depending on the species of carotenoids. As an example, the results of experiments using mice conducted by Nobuo Takasuka et al. of the Research Institute, National Cancer Center (Report of 1996 Meeting on Carotenoid Research) will be shown below. The incidence of lung cancer (ddy mouse lung two-stage carcinogenesis model) was 40% in α-carotene-administered mice, 70% in lutein- or astaxanthin-administered mice and 139% in β-carotene-administered mice, when the incidence in control mice without carotenoid administration was taken as 100%. The incidence of liver cancer (mouse spontaneous liver carcinogenesis model) was 30% in astaxanthin- or fucoxanthin-administered mice, 50% in α-carotene- or lutein-administered mice, 70% in β-carotene-administered mice, and 100% in lycopene-administered mice, when the incidence in control mice without carotenoid administration was taken as 100%. The incidence of skin cancer (mouse skin carcinogenesis model) was 10% in fucoxanthin- or lycopene-administered mice, and 100% in astaxanthin-administered mice, when the incidence in control mice without carotenoid administration was taken as 100%. Comparison of the results on these three carcinogenesis models reveals that lycopene which was highly effective in inhibiting lung cancer and skin cancer is not effective in inhibiting liver cancer; and that astaxanthin which was highly effective in inhibiting liver cancer is not effective in inhibiting skin cancer. Further, as a result of epidemiological tests and clinical tests, it has been reported that, among dietary carotenoids, only lycopene was confirmed as a prophylactic carotenoid against prostate cancer (see Giovannucci, E., Ascherio, A., Rimm, E. B., Stampfer, M. J., Colditz, G. A., Willet, W. C., "Intake of carotenids and retinol in relation to risk of prostate cancer", J. National Cancer Institute 87, 1767-1776, 1995; Vogt, T. M. et al, "Serum lycopene, other serum carotenoids, and risk of prostate cancer in US Blacks and Whites", Am. J. Epidemiol. 155, 1023-1032, 2002). Recently, high prophylactic effect of β-cryptoxanthin on lung cancer has been gradually elucidated (see Yuan, J. M., Stram, D. O., Arakawa, K., Lee, H. P. and Yu M. C., "Dietary cryptoxanthin and reduced risk of lung cancer: the Singapore Chinese Health Study", Cancer Epidemiol. Biomarkers Prev. 12, 890-898, 2003; Mannisto, S. et al, "Dietary carotenoids and risk of lung cancer in a pooled analysis of seven cohort studies", Cancer Epidemiol. Biomarkers Prev. 13, 40-48, 2004). In addition to cancer prophylactic effects, it has been also reported that carotenoids are very likely to be effective in preventing chronic diseases in the cardiovascular system, chronic diseases in the eye such as cataract, and chronic diseases such as osteoporosis. For example, it has been reported that carotenoids which are expected to be effective on chronic diseases in the eye (age-related macular degeneration, cataract, etc.) are lutein and zeaxanthin alone among dietary carotenoids (see Semba, R. D. and Dagnelie, G., "Are lutein and zeaxanthin conditionally essential nutrients for eye health?", Med. Hypotheses 61, 465-472, 2003; Mazaffarieh, M., Sacu, S. and Wedrich, A., "The role of the carotenoids, lutein and zeaxanthin, in protecting against age-related macular degeneration: A review based on controversial evidence", Nutr. J., 2, 20, 2003).

The results described so far indicate that only about 10 out of 700 or more species of carotenoids have been examined for their prophylactic effects on chronic diseases such as cancer in studies actually using animal individuals, and that each carotenoid has characteristic individuality in prophylactic effect on chronic diseases such as cancer. It is believed that the major reason why the number of species of carotenoids actually examined is so mall is because those carotenoids which can be extracted, purified or chemically synthesized in large quantities are limited to the above-mentioned carotenoids.

As a promising means to solve the above problem, a method may be considered in which a carotenoid of interest is mass-produced in carotenoid biosynthesis gene-transferred yeast or *Escherichia coli*. For example, Shimada et al. of Kirin Brewery introduced a carotenoid biosynthesis gene cluster into a food yeast *Candida utilis* which naturally does not biosynthesize carotenoids, expressed the genes and succeeded in synthesizing 7.8 mg/g of lycopene (dry weight) (Shimada, H., Kondo, K., Fraser, P. D., Miura, Y., Saito, T., and Misawa, N., "Increased carotenoid production by the food yeast *Candida utilis* through metabolic engineering of the isoprenoid pathway", Appl. Environ. Microbiol., 64, 2676-2680, 1998). According to the gene recombination technique, it becomes possible to produce such carotenoids that have not been found in nature or found only in trace amounts, by a combination of various biosynthesis genes. For example, Takaichi et al. of Nippon Medical School have succeeded in producing parasiloxanthin (which is only reported to be found in catfish in a trace amount) as a major carotenoid product in a recombinant *E. coli* (Takaichi, S., Sandmann, G., Schnurr, G., Satomi, Y., Suzuki, A., and Misawa, N. "The carotenoid 7,8-dihydro-Ψ end group can be cyclized by the lycopene cyclases from the bacterium *Erwinia uredovora* and the higher plant *Capsicum annuum*", Eur. J. Biochem., 241, 291-296, 1996). There is another report that astaxanthin-β-diglucoside, a "non-natural type" carotenoid not found in nature, was produced in a recombinant *E. coli* (Yokoyama, A., Shizuri, Y.,and Misawa, N., Production of new carotenoids, astaxanthin glucosides, by *Escherichia coli* transformants carrying carotenoid biosynthetic genes. Tetrahed. Lett., 39, 3709-3712, 1998).

The carotenoid biosynthesis genes most commonly used in the preparation of recombinant microorganisms for various carotenoid productions are derived from *Erwinia* bacteria (such as *Erwinia uredovora*; recently, this bacterium is called *Pantoea ananatis*). Six genes have been isolated from *Erwinia* bacteria; they are crtE, crtB, crtI, crtY, crtZ and crtX. The functions of the biosynthesis enzymes encoded by these genes (CrtE, CrtB CrtI, CrtY, CrtZ and CrtX) are shown in FIG. 1 (see Non-Patent Document 1). When biosynthesis of astaxanthin is intended, crtW gene derived from marine bacteria *Paracoccus* [such as *Paracoccus* sp. MBIC 01143 (*Agrobacterium aurantiacum*)] is additionally required (FIG. 1). Five gene have been isolated from *Paracoccus* bacteria; they are crtB, crtI, crtY, crtZ and crtW (see Non-Patent Document 1). The functions of crtB, crtI, crtY and crtZ genes are common in both bacteria. When *Erwinia*- or *Paracoccus*-derived crtE, crtB, crtI and crtY genes have been introduced and expressed in *E. coli*, the *E. coli* biosynthesizes β-carotene. When marine bacterium-derived crtW gene and *Erwinia*- or *Paracoccus*-derived crtZ gene are further introduced and expressed in the above *E. coli*, the recombinant *E. coli* begins to synthesize astaxanthin. Further, when *Erwinia*-derived crtX gene is introduced and expressed in this *E. coli* synthesizing astaxanthin, the recombinant *E. coli* begins to synthesize a "non-natural type" carotenoid, astaxanthin-β-diglucoside (FIG. 1).

As described so far, it is being demonstrated that carotenoid biosynthesis genes can be used to produce "rare" carotenoids which occur only in trace amounts in nature or "non-natural type" carotenoids existence of which has not been confirmed. On the other hand, the carotenoid biosynthesis genes which may be used for this purpose are limited to 25 genes. They are crtM (dehydrosqualene synthase), crtE (gps, al-3) (geranylgeranyl pyrophosphate synthase), crtB (psy, al-2) (phytoene synthase), crtN (dehydrosqualene desaturase), crtP (pdsl) (phytoene desaturase: addition of two double bonds), crtQ (zds) (ζ-carotene desaturase: addition of two double bonds), crtI (derived from *Rhodobacter*) (phytoene desaturase: addition of three double bonds and cis-trans isomerization), crtI (phytoene desaturase: addition of four double bonds and cis-trans isomerization), al-1 (phytoene desaturase: addition of five double bonds and cis-trans isomerization), crtY (crtL-P) (lycopene β-cyclase), crtL-c (lycopene ε-cyclase), crtYm (lycopene β-monocyclase), crtU (β-carotene desaturase), crtZ (β-carotene hydroxylase; β-C3-hydroxylase), crtW (bkt) (β-carotene ketolase; β-C4-oxygenase), crtO (derived from *Synechocystis* sp. PCC6803) (β-carotene monoketolase), crtX (zeaxanthin glucosyltransferase), crtC (hydroxyneurosporene synthase), crtD (methoxyneurosporene desaturase), crtF (hydroxyneurosporene o-methyltransferase), crtA (spheroidene monooxygenase), crtEb (lycopene elongase), crtYe/Yf (decaprenoxanthin synthase), zepl (zeaxanthin epoxydase) and ccs (capsanthin/capsorubin synthase) (see Lee, P. C. and Schmidt-Dannert, C., "Metabolic engineering towards biotechnological production of carotenoids in microorganisms", Appl. Microbiol. Biotechnol. 60, 1-11, 2002; Teramoto, M., Takaichi, S., Inomata, Y., Ikenaga, H. and Misawa, N. "Structural and functional analysis of a lycopene β-monocyclase gene isolated from a unique marine bacterium that produces myxol", FEBS Lett. 545, 120-126, 2003). In order to allow microorganisms such as *E. coli* to produce a wide variety of carotenoids, novel carotenoid biosynthesis genes must be isolated. However, cloning of novel carotenoid biosynthesis genes makes very slow progress. For example, while carotenoids occurring most abundantly in nature are those with β-ionone rings (in FIG. 1, β-carotene, zeaxanthin, canthaxanthin, astaxanthin, etc.), only two genes of enzymes which hydroxylate or oxygenate β-ionone rings have been isolated. They are genes encoding β-ionone ring-3-hydroxylase (β-C3-hydroxylase) (CrtZ) and β-ionone ring-4-ketolase (β-C4-ketolase; β-C4-oxygenase) (CrtW), respectively. These enzyme genes were isolated as early as in 1990 for crtZ and in 1995 for crtW, and analyzed for their functions. It is believed that a gene of β-ionone ring-2-hydroxylase is necessary for synthesizing carotenoids such as nostoxanthin in which the position 2 carbon of the β-ionone ring is hydroxylated. However, though there are some microorganisms producing such carotenoids (see Non-Patent Document 2), nothing has been found to date about such an enzyme or gene. It seems that the reason why the cloning of novel carotenoid biosynthesis genes is difficult is because those carotenoid biosynthesis genes obtainable by expression cloning in *E. coli* or by cloning using homology to existing carotenoid genes have already been obtained and all the remaining genes are not obtainable by these cloning methods.

Carotenoids consisting of carbon and hydrogen alone are called carotene, and carotenoids comprising oxygen-containing functional groups, such as hydroxyl group or keto group, in addition to carbon and hydrogen are called xanthophyll. Carotene and xanthophyll are greatly different in physical property and considerably different in physiological activity in the living body. For example, β-cryptoxanthin is a carotenoid in which one hydroxyl group is introduced at the position 3 carbon of β-carotene. It is known that the intake ratio of β-cryptoxanthin into the living body is 10 times higher than that ratio of β-carotene. β-Cryptoxanthin is a carotenoid which has been especially attracting attention in Japan recently. Data showing its prophylactic effects on large bowel cancer, cervix cancer, esophageal cancer, prostate cancer, rheumatoid and osteoporosis in addition to the above-described lung cancer are being gathered (Yano, M., Report of 2003 Meeting on Carotenoid Research and the above-mentioned Yuan, J. M., Stram, D. O., Arakawa, K., Lee, H. P. and Yu M. C., Cancer Epidemiol. Biomarkers Prev. 12, 890-898, 2003 and Mannisto, S. et al, Cancer Epidemiol. Biomarkers Prev. 13, 40-48, 2004). Such effects are not recognized in β-carotene. A carotenoid in which two hydroxyl groups are introduced at both positions 3 and 3' of β-carotene is zeaxanthin (see FIG. 1). As described above partially, it is known that the physiological activity of zeaxanthin is different from that of β-cryptoxanthin. A carotenoid in which the both methylene groups at positions 4 and 4' of zeaxanthin are converted to keto groups is astaxanthin (see FIG. 1). As described above partially, the physiological activity of astaxanthin in cancer prevention is also greatly different from that of β-carotene.

On the other hand, a carotenoid in which two hydroxyl groups are further introduced at both positions 2 and 2' of zeaxanthin is nostoxanthin. Generally, carotenoids such as nostoxanthin in which two hydroxyl groups are introduced at positions 2 and 2' of β-ionone rings occur only in trace amounts in nature, and it is impossible to produce them in large quantities. Thus, prophylactic studies against various chronic diseases such as cancer cannot be conducted. The enzyme that introduces hydroxyl groups at positions 3 and 3' of β-ionone rings is CrtZ. However, no CrtZ proteins having a 49% or less identity with the *Erwinia uredovora*-derived CrtZ reported in a paper in 1990 for the first time (Misawa, N., Nakagawa, M., Kobayashi, K., Yamano, S., Izawa, Y., Nakamura, K., and Harashima, K., J. Bacteriol. 172, 6704-6712, 1990) have been isolated to date. Among the CrtZ proteins which have been confirmed to have the same function, the enzyme that has the highest homology to the *Erwinia uredovora*-derived CrtZ is a *Paracoccus zeaxanthinifaciens* (old designation: *Flavobacterium* sp. R1534)-derived CrtZ (Pasamontes, L., Hug, D., Tessier, M., Hohmann, H. P., Schierle, J., and van Loon, A. P., Gene 185, 35-41, 1997) with a 50% identity.

(Non-Patent Document 1) Misawa, N., Satomi, Y., Kondo, K., Yokoyama, A., Kajiwara, S., Saito, T., Ohtani, T., and Miki, W., "Structure and functional analysis of a marine bacterial carotenoid biosynthesis gene cluster and astaxanthin biosynthetic pathway proposed at the gene level", J. Bacteriol., 177, 6575-6584, 1995)

(Non-Patent Document 2) Yokoyama, A., Miki, W., Izumida, H., and Shizuri, Y., "New trihydroxy-keto-carotenoids isolated from an astaxanthin-producing marine bacterium", Biosci. Biotech. Bioche., 60, 200-203, 1996)

DISCLOSURE OF THE INVENTION

Problem for Solution by the Invention

It is an object of the present invention to isolate a gene encoding an enzyme that hydroxylates position 2 of β-ionone ring (β-ionone ring-2-hydroxylase). Further, the present invention aims at providing a method of producing carotenoids in which position 2 of the β-ionone ring is hydroxylated (such as 2-hydroxyastaxanthin or nostoxanthin), using a recombinant microorganism in which the above gene is introduced and expressed.

It is another object of the present invention to isolate a gene encoding a carotenoid biosynthesis related enzyme (such as enzyme that hydroxylates position 3 of β-ionone ring; β-ionone ring-3-hydroxylase) with a low homology to existing genes. Further, the present invention aims at providing a method of producing carotenoids in which position 3 of the β-ionone ring is hydroxylated (such as astaxanthin or zeaxanthin), using a recombinant microorganism in which the above gene is introduced and expressed.

Means to Solve the Problem

The present inventors paid attention to the fact that a marine bacterium *Brevundimonas* sp. strain SD-212 (MBIC 03018) is capable of producing carotenoids such as 2-hydroxyastaxanthin and 2-hydroxyadonixanthin in which position 2 of the β-ionone ring is hydroxylated. As a result of intensive and extensive researches, the present inventors have succeeded for the first time in the world in isolating a gene encoding an enzyme that hydroxylates position 2 of the β-ionone ring (β-ionone ring-2-hydroxylase). Among the carotenoid biosynthesis gene cluster encoding the above-mentioned enzyme, the present inventors have found genes encoding an enzyme that hydroxylate position 3 of the β-ionone ring (β-ionone ring-3-hydroxylase) and a geranylgeranyl pyrophosphate (GGPP) synthase, with extremely low homologies to existing genes. The catalytic functions of these enzymes could be confirmed.

First, a cosmid library was prepared in *E. coli* using the chromosomal DNA of *Brevundimonas* sp. strain SD-212. In the preparation of a cosmid library in *E. coli* using the chromosomal DNA of a carotenoid-producing *Erwinia* bacterium (such as *Erwinia uredovora*), yellow colonies (carotenoid-producing *E. coli*) are obtained on plates at this stage. Therefore, a carotenoid biosynthesis gene cluster can be obtained easily. However, no *E. coli* colonies showing color change were obtained from the cosmid library of *Brevundimonas* sp. strain SD-212. Then, a cosmid library of *Brevundimonas* sp. strain SD-212 was prepared in a recombinant *E. coli* (yellow colonies) which produces zeaxanthin as a result of introduction of *Erwinia uredovora*-derived crtE, crtB, crtI, crtY and crtZ genes (see FIG. 1). In the resultant cosmid library, no colonies showing color change were obtained. Then, 700 colonies were cultured and subjected to examination with HPLC-PDA (photodiode detector) to see whether a novel carotenoid is produced in addition to the control (zeaxanthin). As a result, no colonies produced a novel carotenoid. Therefore, the inventors concluded that it is impossible to conduct expression cloning of carotenoid biosynthesis genes of *Brevundimonas* sp. strain SD-212.

Subsequently, the present inventors have found that phytoene desaturase (crtI) genes have two conserved domains among carotenoid-producing bacteria and designed PCR primers choosing these domains. Using the resultant primers, PCR was performed with the chromosomal DNA of *Brevundimonas* sp. strain SD-212 as a template. As a result, a 1.1 kb DNA fragment was amplified. The nucleotide sequence of this fragment was determined and found to be a partial sequence of crtI. Colony hybridization of strain SD-212 cosmid library was performed with the partial sequence of crtI as a probe. Several positive colonies were obtained. Plasmid DNA was prepared from the positive colonies and subjected to Southern hybridization, to thereby obtain a positive 12 kb EcoRI DNA fragment. The nucleotide sequence of this 12 kb EcoRI fragment was determined. Fortunately, it has become clear that a carotenoid biosynthesis gene cluster [seven open reading frames (ORFs) having homology to existing six crt genes and one idi gene] is present within this fragment. Further, it was found that five unknown ORFs are present within this 12 kb EcoRI fragment. For forced expression of all of these 12 ORFs in *E. coli* by the fusion protein method using the lac promoter in *E. coli* vector pUC18 and a lacZ leader sequence, constructs were prepared. Then, using *Erwinia*- or *Paracoccus*-derived crt genes, functional analysis of these 12 ORFs was performed in *E. coli* cells producing various carotenoids as hosts. The results revealed that the six ORFs having homology to existing carotenoid biosynthesis (crt) genes are carotenoid biosynthesis (crt) genes having functions similar to those of the existing carotenoid biosynthesis (crt) genes. Surprisingly, however, it was found that crtZ gene which is one of these carotenoid biosynthesis genes encodes a β-ionone ring-3-hydroxylase having only a 46% or less identity with any of the existing CrtZ proteins at the amino acid sequence level. Further, it was also found that crtE gene which is one of these carotenoid biosynthesis genes encodes a geranylgeranyl pyrophosphate (GGPP) synthase having only a 39% or less identity with any of the existing CrtE proteins at the amino acid sequence level. Further, the present inventors have ascertained that one of the unknown ORFs (ORF11) is a gene encoding a β-ionone ring-2-hydroxylase. Thus, the present invention has been achieved.

The present invention has been achieved based on the above-described findings.

The present invention provides the following (1) to (17).

(1) A peptide selected from the following (a), (b), (c) or (d):
(a) a peptide consisting of the amino acid sequence as shown in SEQ ID NO: 4;
(b) a peptide which consists of the amino acid sequence as shown in SEQ ID NO: 4 having addition, deletion or substitution of one or a plurality of amino acids. and has β-ionone ring-2-hydroxylase activity;
(c) a peptide which consists of an amino acid sequence having a 50% or more identity with the amino acid sequence as shown in SEQ ID NO: 4 and has β-ionone ring-2-hydroxylase activity; or
(d) a bacterium-derived peptide which is encoded by a DNA consisting of the nucleotide sequence as shown in SEQ ID NO: 3 or a DNA hybridizable to a complementary DNA to the above DNA under stringent conditions and has β-ionone ring-2-hydroxylase activity.

(2) A gene encoding a peptide selected from the following (a), (b), (c) or (d):
(a) a peptide consisting of the amino acid sequence as shown in SEQ ID NO: 4;
(b) a peptide which consists of the amino acid sequence as shown in SEQ ID NO: 4 having addition, deletion or substitution of one or a plurality of amino acids and has β-ionone ring-2-hydroxylase activity;
(c) a peptide which consists of an amino acid sequence having a 50% or more identity with the amino acid sequence as shown in SEQ ID NO: 4 and has β-ionone ring-2-hydroxylase activity; or
(d) a bacterium-derived peptide which is encoded by a DNA consisting of the nucleotide sequence as shown in SEQ ID NO: 3 or a DNA hybridizable to a complementary DNA to the above DNA under stringent conditions and has β-ionone ring-2-hydroxylase activity.

(3) A microorganism obtainable by introducing the gene according to (2) thereinto, wherein the microorganism is capable of introducing a hydroxyl group at the position 2 carbon of β-ionone ring.

(4) A microorganism obtainable by introducing the gene according to (2) and other carotenoid biosynthesis genes thereinto, wherein the microorganism is capable of introducing a hydroxyl group at the position 2 carbon of β-ionone ring.

(5) The microorganism according to (4), wherein the other carotenoid biosynthesis genes are all or a part of a gene cluster required for synthesizing β-ionone ring-containing carotenoids from farnesyl pyrophosphate.

(6) The microorganism according to any one of (3) to (5), wherein the microorganism is *Escherichia coli*.

(7) A method of preparing a hydroxylated carotenoid, comprising culturing the microorganism according to any one of (3) to (6) in a medium and obtaining from the resultant culture or cells a carotenoid which is hydroxylated at the position 2 carbon of its β-ionone ring.

(8) The method according to (7), wherein the carotenoid which is hydroxylated at the position 2 carbon of its β-ionone ring is β,β-carotene-2-ol (2-hydroxy-β-carotene), β,β-carotene-2,2'-diol (2,2'-dihydroxy-β-carotene), caloxanthin (2-hydroxyzeaxanthin), nostoxanthin (2,2'-dihydroxyzeaxanthin), 2-hydroxy-β,β-carotene-4,4'-dione (2-hydroxycanthaxanthin), 2,2'-dihydroxy-β,β-carotene-4,4'-dione (2,2'-dihydroxycanthaxanthin), 2-hydroxyastaxanthin or 2,3,2',3'-tetrahydroxy-β,β-carotene-4,4'-dione (2,2'-dihydroxyastaxanthin). (9) 2,2'-dihydroxy-β,β-carotene-4,4'-dione (2,2'-dihydroxycanthaxanthin) represented by the following chemical formula (I):

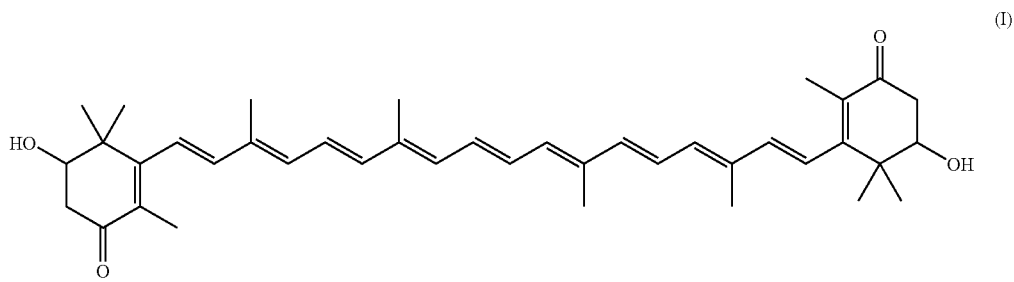

(10) An antioxidant comprising 2,2'-dihydroxy-β,β-carotene-4,4'-dione (2,2'-dihydroxycanthaxanthin) or 2-hydroxy-β, β-carotene-4,4'-dione (2-hydroxycanthaxanthin) as an active ingredient.

(11) A gene encoding a peptide selected from the following (e), (f) or (g):
(e) a peptide consisting of the amino acid sequence as shown in SEQ ID NO: 30;
(f) a peptide which consists of the amino acid sequence as shown in SEQ ID NO: 30 having addition, deletion or substitution of one or a plurality of amino acids and has β-ionone ring-3-hydroxylase activity; or
(g) a bacterium-derived peptide which is encoded by a DNA consisting of the nucleotide sequence as shown in SEQ ID NO: 29 or a DNA hybridizable to a complementary DNA to the above DNA under stringent conditions and has β-ionone ring-3-hydroxylase activity.

(12) A microorganism obtainable by introducing the gene according to (11) thereinto, wherein the microorganism is capable of introducing a hydroxyl group at the position 3 carbon of β-ionone ring.

(13) A microorganism obtainable by introducing the gene according to (11) and other carotenoid biosynthesis genes thereinto, wherein the microorganism is capable of introducing a hydroxyl group at the position 3 carbon of β-ionone ring.

(14) The microorganism according to (13), wherein the other carotenoid biosynthesis genes are all or a part of a gene cluster required for synthesizing β-ionone ring-containing carotenoids from farnesyl pyrophosphate.

(15) The microorganism according to any one of (12) to (14), wherein the microorganism is *Escherichia coli*.

(16) A method of preparing a hydroxylated carotenoid, comprising culturing the microorganism according to any one of (12) to (15) in a medium and obtaining from the resultant culture or cells a carotenoid which is hydroxylated at the position 3 carbon of its β-ionone ring.

(17) A gene encoding a peptide selected from the following (h), (i) or o):

(h) a peptide consisting of the amino acid sequence as shown in SEQ ID NO: 32;

(i) a peptide which consists of the amino acid sequence as shown in SEQ ID NO: 32 having addition, deletion or substitution of one or a plurality of amino acids and has geranylgeranyl pyrophosphate synthase activity; or (j) a bacterium-derived peptide which is encoded by a DNA consisting of the nucleotide sequence as shown in SEQ ID NO: 31 or a DNA hybridizable to a complementary DNA to the above DNA under stringent conditions and has geranylgeranyl pyrophosphate synthase activity.

Hereinbelow, the present invention will be described in detail.

1. Gene Source: Marine Bacterium *Brevundimonas* sp. strain SD-212 (MBIC 03018)

The marine bacterium *Brevundimonas* sp. strain SD-212 (SD212; MBIC 03018) which was the source for genes of interest is α-proteobacterium isolated from the seawater around Volcano Islands belonging to Ogasawara Islands. GC content is 67.1 (mol) %. Yokoyama et al. of Marine Biotechnology Institute Co., Ltd. have reported that carotenoids produced by this marine bacterium are 2(2')-hydroxylated carotenoids such as 2-hydroxyastaxanthin and 2-hydroxyadonixanthin (see Non-Patent Document 2). By the way, this bacterium is published and released by Marine Biotechnology Institute Co., Ltd. The 16S rDNA sequence and gyrB gene sequence of this bacterium are registered at GenBank/DDBJ under Accession Nos. AB016849 and AB014993, respectively.

2. Estimate of the Carotenoid Biosynthesis Pathway in the Marine Bacterium *Brevundimonas* sp. strain SD-212

The 2(2')-hydroxylated carotenoids produced by the marine bacterium *Brevundimonas* sp. strain SD-212 (MBIC 03018) are analyzed in detail by Yokoyama et al. (see Non-Patent Document 2). They are 2,3,2',3'-tetrahydroxy-β,β-carotene-4,4'-dione, 2,3,2',3'-tetrahydroxy-β,β-carotene-4-one, 2-hydroxyastaxanthin (2,3, 3'-trihydroxy-β,β-carotene-4,4'-dione), 2-hydroxyadonixanthin (2,3, 3'-trihydroxy-β,β-carotene-4-one), and erythroxanthin (3,2',3'-trihydroxy-β,β-carotene-4-one) (see FIG. 2). It has been also confirmed that astaxanthin and adonixanthin (4-ketozeaxanthin) are also present in strain SD-212 as precursors. Given the existence of a novel enzyme that introduces a hydroxyl group at position 2 of the β-ionone ring (β-ionone ring-2-hydroxylase; designated "CrtV"), a biosynthesis pathway using this enzyme and a combination of existing Crt proteins, for all of the above carotenoids may be estimated as described in FIG. 2.

3. Gene Encoding β-Jonone Ring-2-Hydroxylase (The First Gene of the Invention)

The present invention includes the peptide of the following (a), (b), (c) or (d).

(a) a peptide consisting of the amino acid sequence as shown in SEQ ID NO: 4;

(b) a peptide which consists of the amino acid sequence as shown in SEQ ID NO: 4 having addition, deletion or substitution of one or a plurality of amino acids and has β-ionone ring-2-hydroxylase activity;

(c) a peptide which consists of an amino acid sequence having a 50% or more identity with the amino acid sequence as shown in SEQ ID NO: 4 and has β-ionone ring-2-hydroxylase activity; or (d) a bacterium-derived peptide which is encoded by a DNA consisting of the nucleotide sequence as shown in SEQ ID NO: 3 or a DNA hybridizable to a complementary DNA to the above DNA under stringent conditions and has β-ionone ring-2-hydroxylase activity.

The peptide of (a) is a *Brevundimonas* sp. strain SD-212-derived peptide (sometimes called "CrtV") having β-ionone ring-2-hydroxylase activity and consisting of a 257 amino acid sequence.

The peptide of (b) is a peptide of (a) into which mutations that would not eliminate β-ionone ring-2-hydroxylase activity have been introduced. Such mutations include mutations occurring spontaneously in nature and artificial mutations. Examples of means to cause artificial mutations include, but are not limited to, site-specific mutagenesis (Nucleic Acids Res. 10, 6487-6500, 1982). The number of mutated amino acids is not particularly limited as long as β-ionone ring-2-hydroxylase activity is retained. Usually, the number of mutated amino acids is within 30, preferably within 20, more preferably within 10, and most preferably within 5.

The peptide of (c) is a peptide which consists of an amino acid sequence having a 50% or more identity (ratio of identical amino acid sequence) with the peptide of (a) when the entire regions of both peptides are compared, and has β-ionone ring-2-hydroxylase activity. The "50% or more identity" is based on the following reason. Briefly, as described earlier in "Background Art", since the gene encoding an *Erwinia uredovora*-derived β-ionone ring-3-hydroxylase (CrtZ) was elucidated for the first time 14 years ago, structures of various CrtZ peptides have been elucidated. Among the CrtZ proteins which have been confirmed to have the same catalytic function, the enzyme that has the lowest homology to this *Erwinia uredovora*-derived CrtZ is a *Paracoccus zeaxanthinifaciens* (old designation: *Flavobacterium* sp. R1534)-derived CrtZ (Pasamontes, L., Hug, D., Tessier, M., Hohmann, H. P., Schierle, J., and van Loon, A. P., Gene 185, 35-41, 1997) with a 50% identity. Further, as described later, no CrtZ proteins have a 50% or more identity with the *Brevundimonas* sp. strain SD-212-derived peptide (CrtZ) consisting of a 161 amino acid sequence having β-ionone ring-3-hydroxylase activity as a result of search through DDBJ and GenBank databases. The CrtZ protein which has the highest identity with the *Brevundimonas* sp. strain SD-212-derived CrtZ is a CrtZ derived from *Erwinia herbicola* (recently, called *Pantoea agglomerans*) (JJBJ/GenBank accession no. M87280) with a 46% identity. Besides, according to the present invention, it was made clear that the catalytic functions of these two CrtZ proteins are identical. Taking into consideration that β-ionone ring-2-hydroxylase (CrtV) and β-ionone ring-3-hydroxylase (CrtZ) are enzymes very similar in nature, enzymes which consist of an amino acid sequence having a 50% or more identity with the peptide of (a) above and have β-ionone ring-2-hydroxylase activity (identical catalytic function) will surely be found in the future in microorganisms producing carotenoids in which position 2 of the β-ionone ring is hydroxylated. For example, such enzymes will be found by analyzing the genome of a bacterium producing carotenoids in which position 2 of the 3-ionone ring is hydroxylated [e.g. Erthrobacter sp. Strain PC6 (MBIC 02351)]. Further, the amino acid sequences of such enzymes which will be thus found in nature may be mutated by the method described earlier.

The peptide of (d) is a bacterium-derived peptide which is obtainable by using DNA hybridization and has β-ionone ring-2-hydroxylase activity. The "stringent conditions" in the peptide of (c) means conditions which allow specific hybridization alone and eliminate non-specific hybridization. Usually, such conditions are about "1×SSC, 0.1% SDS, 37° C."; preferably about "0.5×SSC, 0.1% SDS, 42° C."; and more preferably about "0.2×SSC, 0.1% SDS, 65° C.". The DNA obtainable by such hybridization usually has a high homology to the DNA represented by the nucleotide sequence as shown in SEQ ID NO: 3. The term "high homology" refers to a 60% or more homology, preferably a 75% or more homology, and still more preferably a 90% or more homology.

The gene of the present invention may be obtained, for example, as described below. First, a cosmid library of the marine bacterium Brevundimonas sp. strain SD-212 is prepared in E. coli. Then, the gene of the present invention may be obtained by such methods as colony hybridization using a homologous sequence of a carotenoid biosynthesis gene as described in Example 7 or PCR cloning.

Escherichia coli carrying plasmid p5Bre2-15 which was prepared by inserting into E. coli vector pBluescript II KS- a 12 kb EcoRI DNA fragment comprising the carotenoid biosynthesis gene cluster of Brevundimonas sp. strain SD-212 containing the gene of the invention, i.e., β-ionone ring-2-hydroxylase (crtV) gene, has been deposited at the International Patent Organism Depository, National Institute of Advanced Industrial Science and Technology under Accession No. β-19580.

4. Gene Encoding β-Ionone Ring-3-Hydroxylase (The Second Gene of the Invention)

The present invention includes the peptide of the following (e), (f) or (g).

(e) a peptide consisting of the amino acid sequence as shown in SEQ ID NO: 30;
(f) a peptide which consists of the amino acid sequence as shown in SEQ ID NO: 30 having addition, deletion or substitution of one or a plurality of amino acids and has β-ionone ring-3-hydroxylase activity; or
(g) a bacterium-derived peptide which is encoded by a DNA consisting of the nucleotide sequence as shown in SEQ ID NO: 29 or a DNA hybridizable to a complementary DNA to said DNA under stringent conditions and has β-ionone ring-3-hydroxylase activity.

The peptide of (e) is a Brevundimonas sp. strain SD-212-derived peptide (sometimes called "CrtZ") having β-ionone ring-3-hydroxylase activity and consisting of a 161 amino acid sequence.

The peptide of (f) is a peptide of (e) into which mutations that would not eliminate β-ionone ring-3-hydroxylase activity have been introduced. Such mutations include mutations occurring spontaneously in nature and artificial mutations. Means to cause artificial mutations is as described above.

The peptide of (g) is a bacterium-derived peptide which is obtainable by using DNA hybridization and has β-ionone ring-3-hydroxylase activity. The "stringent conditions" in the peptide of (g) are as described above.

5. Gene Encoding Geranylgeranyl Pyrophosphate Synthase (The Third Gene of the Invention)

The present invention also includes a gene encoding the following peptide (h), (i) ore).

(h) a peptide consisting of the amino acid sequence as shown in SEQ ID NO: 32;
(i) a peptide which consists of the amino acid sequence as shown in SEQ ID NO: 32 having addition, deletion or substitution of one or a plurality of amino acids and has geranylgeranyl pyrophosphate synthase activity; or
(j) a bacterium-derived peptide which is encoded by a DNA consisting of the nucleotide sequence as shown in SEQ ID NO: 31 or a DNA hybridizable to a complementary DNA to the above DNA under stringent conditions and has geranylgeranyl pyrophosphate synthase activity.

The peptide of (h) is a Brevundimonas sp. strain SD-212-derived peptide (sometimes called "CrtE") having geranylgeranyl pyrophosphate synthase activity and consisting of a 298 amino acid sequence.

The peptide of (i) is a peptide of (h) into which mutations that would not eliminate geranylgeranyl pyrophosphate synthase activity have been introduced. Such mutations include mutations occurring spontaneously in nature and artificial mutations. Means to cause artificial mutations is as described above.

The peptide of (g) is a bacterium-derived peptide which is obtainable by using DNA hybridization and has geranylgeranyl pyrophosphate synthase activity. The "stringent conditions" in the peptide of (j) are as described above.

6. Microorganism Capable of Introducing a Hydroxyl Group at the Position 2(2') or 3(3') Carbon of β-Ionone Ring The present invention includes a microorganism obtainable by introducing thereinto the β-ionone ring-2-hydroxylage gene described in 3 above, wherein the microorganism is capable of introducing a hydroxyl group at the position 2 carbon of β-ionone ring.

The present invention also includes a microorganism obtainable by introducing thereinto the β-ionone ring-3-hydroxylage gene described in 4 above, wherein the microorganism is capable of introducing a hydroxyl group at the position 3 carbon of β-ionone ring.

Not only the gene of the invention but also other carotenoid biosynthesis genes are often introduced into a microorganism. However, when the microorganism inherently has other carotenoid biosynthesis genes, other carotenoid biosynthesis genes may not be introduced or only a part of them is introduced.

Examples of host microorganisms include, but are not limited to, E. coli.

The "other carotenoid biosynthesis genes" include all or a part of a gene cluster required for synthesizing β-ionone ring-containing carotenoids from farnesyl pyrophosphate (FPP). Specific examples of such a gene cluster include, but are not limited to, crtE encoding an enzyme that synthesizes geranylgeranyl pyrophosphate (GGPP) from FPP, crtB encoding an enzyme that synthesizes phytoene from two molecules of GGPP, crtI encoding an enzyme that synthesizes lycopene from phytoene, crtY (usually, derived from Erwinia bacteria) encoding an enzyme that synthesizes β-carotene from lycopene, and crtW (usually, derived from Paracoccus bacteria) encoding β-ionone ring -4-ketolase.

When all or a part of such a gene cluster is integrated into an appropriate expression vector and then introduced into a host microorganism, the recombinant microorganism begins to produce β-ionone ring-containing carotenoids. (Every microorganism is capable of producing the substrate FPP. Although some microorganisms produce only a small amount of GGPP, every microorganism is also capable of producing GGPP.) When the first gene of the invention (crtV encoding β-ionone ring-2-hydroxylase) is further introduced and expressed in the above recombinant microorganism producing β-ionone ring-containing carotenoids, the microorganism begins to produce carotenoids in which a hydroxyl group is introduced at position 2(2'). When the second gene of the invention (crtZ encoding β-ionone ring-3-hydroxylase) is further introduced and expressed in the above recombinant microorganism producing β-ionone ring-containing carotenoids, the microorganism begins to produce carotenoids in which a hydroxyl group is introduced at position 3(3').

Information about vectors of various microorganisms such as E. coli or yeast, and methods of introduction/expression of exogenous genes are disclosed in a number of experimental manuals (e.g., Sambrook, J., Russel, D. W., "Molecular Cloning: A Laboratory Manual, 3$^{rd}$ Edition", CSHL Press, 2001). Selection of vectors and introduction/expression of genes may be performed according to those manuals.

7. Method of Preparing 2(2')- or 3(3')-Hydroxylated Carotenoids

The present invention also includes a method of preparing a hydroxylated carotenoid, comprising culturing the above-described microorganism in a medium and obtaining from the resultant culture or cells a carotenoid in which the position 2 or 3 carbon of its β-ionone ring is hydroxylated.

Specific examples of carotenoids which are hydroxylated at the position 2 carbon of the β-ionone ring include, but are not limited to, β,β-carotene-2-ol (2-hydroxy-β-carotene), O,β-carotene-2,2'-diol (2,2'-dihydroxy-β-carotene), caloxanthin (2-hydroxyzeaxanthin), nostoxanthin (2,2'-dihydroxyzeaxanthin), 2-hydroxy-β,β-carotene-4,4'-dione (2-hydroxycanthaxanthin), 2,2'-dihydroxy-β,β-carotene-4,4'-dione (2,2'-dihydroxycanthaxanthin), 2-hydroxyastaxanthin and 2,3,2',3'-tetrahydroxy-β,β-carotene-4,4'-dione (2,2'-dihydroxyastaxanthin). Of the above carotenoids, 2-hydroxy-β,β-carotene-4,4'-dione (2-hydroxycanthaxanthin) and 2,2'-dihydroxy-β,β-carotene-4,4'-dione (2,2'-dihydroxycanthaxanthin) (especially the latter) have been demonstrated to have strong inhibitory effects on peroxidation of lipids as a result of in vitro experiments.

Specific examples of carotenoids which are hydroxylated at the position 3 carbon of the β-ionone ring include, but are not limited to, β-cryptoxanthin, zeaxanthin, caloxanthin (2-hydroxyzeaxanthin), nostoxanthin (2,2'-dihydroxyzeaxanthin), 2-hydroxyastaxanthin and 2,3,2',3'-tetrahydroxy-β, β-carotene-4,4'-dione (2,2'-dihydroxyastaxanthin).

8. Antioxidant

Since 2-hydroxy-β, β-carotene-4,4'-dione and 2,2'-dihydroxy-β, β-carotene-4,4'-dione have strong inhibitory effects on peroxidation of lipids as described above, they may be used as an antioxidant for lipids, or even as an antioxidant for substances in general.

The antioxidant of the invention may be prepared by simply diluting the above-mentioned two carotenoids (active ingredients) with water. Preferably, the carotenoids are prepared into emulsions. Emulsions may be prepared by mixing and emulsifying aqueous components and oil-soluble components by conventional methods. Examples of aqueous components which may be used for this purpose include gallic acid, ascorbic acid, gums and vitamin P (flavonoids). Examples of oil-soluble components which may be used for this purpose include glycerin fatty acid ester and fats and oils such as rapeseed oil, soybean oil or corn oil. The contents of the above-mentioned two carotenoids in the antioxidant of the invention may be selected freely considering the product to which the antioxidant is to be added. Preferably, the content is 0.05-5%.

The antioxidant of the invention is useful mainly as an antioxidant component for foods, cosmetics and pharmaceuticals because of its safety and ability to inhibit oxidation. The doses of the above-mentioned two carotenoids as an antioxidant may vary depending on the product to which the antioxidant is to be added. For example, the carotenoid may be added at about 0.1 g per kg of foods and at about 0.05 g per kg of cosmetics.

Although the antioxidant of the invention produces sufficient effect when used alone, the antioxidant may be used in combination with conventional natural antioxidants (e.g., antioxidant whose active ingredient is tocopherol).

The SEQ ID NOS in the SEQUENCE LISTING of the present specification represent the following sequences.

SEQ ID NO: 1: a partial sequence of the crtI gene of Brevundimonas sp. strain SD-212.

SEQ ID NO: 2: the sequence of a 12 kb fragment cut out from pCos5-2 with EcoRI.

SEQ ID NO: 3: the sequence of ORF11 (presumed to be a β-ionone ring-2-hydroxylase gene) contained in the above-mentioned EcoRI fragment.

SEQ ID NO: 4: the amino acid sequence encoded by ORF11.

SEQ ID NO: 5: a primer (forward) for amplifying ORF1.
SEQ ID NO: 6: a primer (reverse) for amplifying ORF1.
SEQ ID NO: 7: a primer (forward) for amplifying crtW.
SEQ ID NO: 8: a primer (reverse) for amplifying crtW.
SEQ ID NO: 9: a primer (forward) for amplifying crtY.
SEQ ID NO: 10: a primer (reverse) for amplifying crtY.
SEQ ID NO: 11: a primer (forward) for amplifying crtI.
SEQ ID NO: 12: a primer (reverse) for amplifying crtI.
SEQ ID NO: 13: a primer (forward) for amplifying crtB.
SEQ ID NO: 14: a primer (reverse) for amplifying crtB.
SEQ ID NO: 15: a primer (forward) for amplifying ORF6.
SEQ ID NO: 16: a primer (reverse) for amplifying ORF6.
SEQ ID NO: 17: a primer (forward) for amplifying ORF7.
SEQ ID NO: 18: a primer (reverse) for amplifying ORF7.
SEQ ID NO: 19: a primer (forward) for amplifying crtE.
SEQ ID NO: 20: a primer (reverse) for amplifying crtE.
SEQ ID NO: 21: a primer (forward) for amplifying idi.
SEQ ID NO: 22: a primer (reverse) for amplifying idi.
SEQ ID NO: 23: a primer (forward) for amplifying crtZ.
SEQ ID NO: 24: a primer (reverse) for amplifying crtZ.
SEQ ID NO: 25: a primer (forward) for amplifying ORF11.
SEQ ID NO: 26: a primer (reverse) for amplifying ORF11.
SEQ ID NO: 27: a primer (forward) for amplifying ORF12.
SEQ ID NO: 28: a primer (reverse) for amplifying ORF12.
SEQ ID NO: 29: the sequence of crtZ (presumed to be a β-ionone ring-3-hydroxylase gene) contained in the above-mentioned EcoRI fragment.

SEQ ID NO: 30: the amino acid sequence encoded by crtZ.
SEQ ID NO: 31: the sequence of crtE (presumed to be a geranylgeranyl pyrophosphate synthase gene) contained in the above-mentioned EcoRI fragment.

SEQ ID NO: 32: the amino acid sequence encoded by crtE.

Effect of the Invention

Many of those carotenoids in which the 2(2') carbon of the β-ionone ring is hydroxylated occur only in trace amounts in nature, and some have not yet been discovered. According to the present invention, it becomes possible to produce such carotenoids in large quantities. Further, the present invention also provides a gene capable of producing carotenoids in which the 3(3') carbon of the β-ionone ring is hydroxylated and a gene which synthesizes a carotenoid precursor geranylgeranyl pyrophosphate.

BEST MODE FOR CARRYING OUT THE INVENTION

Figure 1:
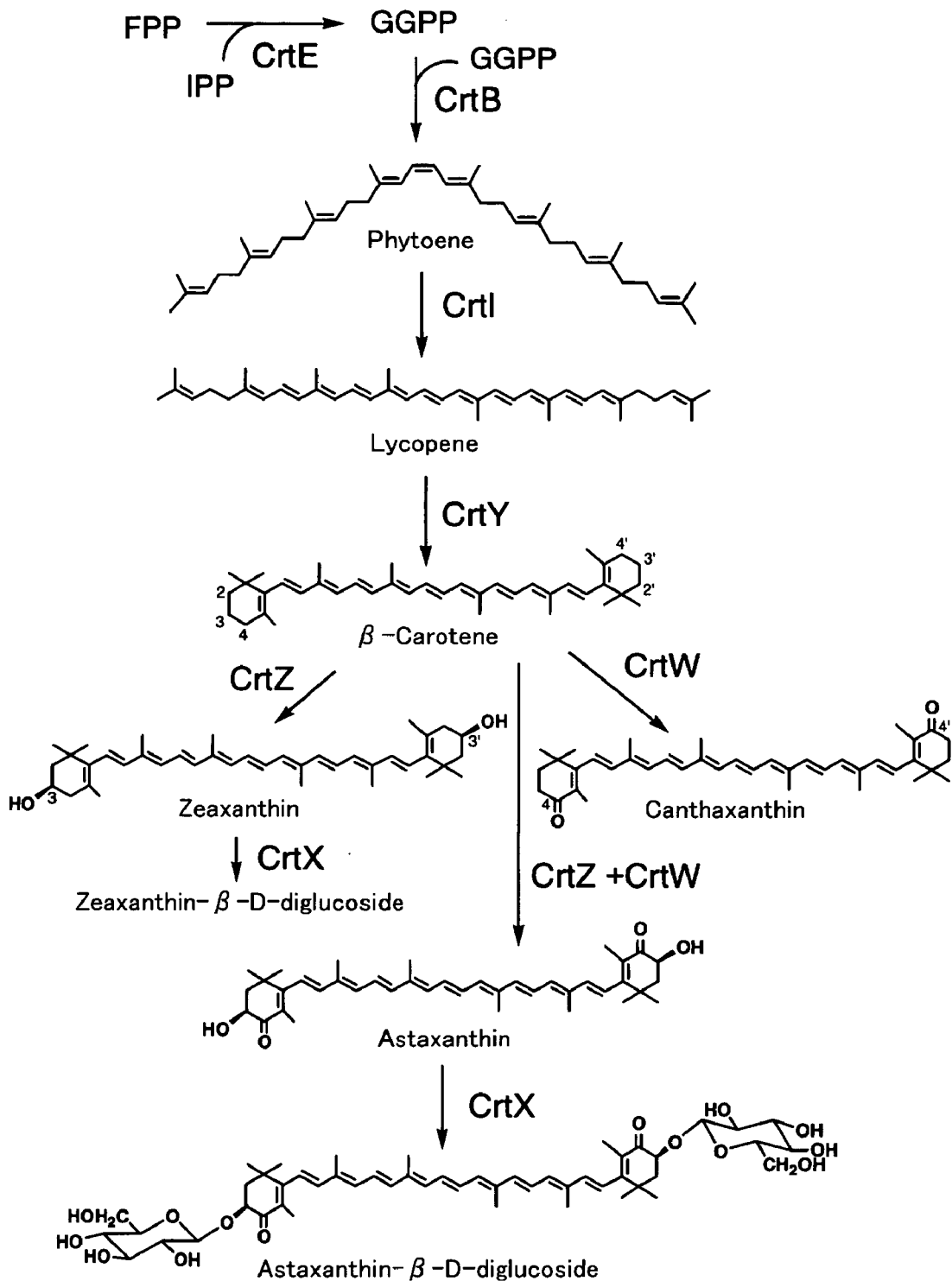
FIG. 1 is a diagram showing the functions and synthesis pathway of existing carotenoid biosynthesis genes (enzymes).

Herein below, the present invention will be described in more detail with reference to the following Examples. However, the present invention is not limited to these Examples.

EXAMPLE 1

Strains, Plasmids and Growth Conditions

The strains and plasmids used in the invention are shown in Table 1. The strains were cultured at 30° C. in LB (Luria-Bertani) medium or 2×YT medium (Sambrook et al., 1989). When necessary, ampicillin (Ap, 100 µg/ml) or chloramphenicol (Cm, 20 µg/ml) was added to the medium.

A plasmid for canthaxanthin production (pAC-Cantha) and a plasmid for astaxanthin and adonixanthin (4-ketozeaxanthin) production (pAC-Asta) were constructed as described below.

Briefly, *Paracoccus* sp. MBIC 01143 (*Agrobacterium aurantiacum*)-derived crtW gene was synthesized so that the codon usage is consistent with in GAP gene in yeast *Candida utilis*. The amino acid sequence encoded by the resultant crtW was made identical with the amino acid sequence of the original CrtW. This method is described previously (Miura et al., 1998). With this totally synthesized crtW sequence as a template, PCR was performed using H1437 primer [containing AvaI site (underlined) and SD sequence (positions 10-15 of H1437)] and H1438 primer [containing NotI site (underlined)]. The resultant PCR product was digested with AvaI and NotI to obtain a 0.76 kb AvaI-crtW-NotI fragment.

```
H1437:
5'-GTCCCGAGAAGGAGGCTAGATATGTCCGCTCACGCTTTGC-3'
(SEQ ID NO: 33)

H1438:
5'-CGGCGGCCGCCCGGGACTAAGCGGTGTCACCCTTGGTTCT-3'
(SEQ ID NO: 34)
```

With plasmid pCAR16 (Misawa et al., 1990) as a template, PCR was performed using H1431 primer [containing NotI site (underlined) and SD sequence (positions 16-21 of H1431)] and H1432 primer [containing SalI site (underlined)]. The resultant PCR product was digested with NotI and SalI to obtain a 1.1 kb NotI-crtE-SalI fragment.

```
H1431:
5'-ATGCGGCCGCTTATAAGGACAGCCCGAATG-3'
(SEQ ID NO: 35)

H1432:
5'-CAGTCGACATCCTTAACTGACGGCAGCGAG-3'
(SEQ ID NO: 36)
```

The above-described 0.76 kb AvaI-crtW-NotI fragment and 1.1 kb NotI-crtE-SalI fragment were ligated to each other via the NotI sites and then ligated to a large fragment containing crtY, crtI and crtB which had been obtained by AvaI/SalI digestion of pACCAR16ΔcrtX, to thereby obtain plasmid pAC-Cantha.

Subsequently, the above-described 0.76 kb AvaI-crtW-NotI fragment and 1.1 kb NotI-crtE-SalI fragment were ligated to each other via the NotI sites in the same manner as described above, and then ligated to a large fragment containing crtY, crtI, crtB and crtZ which had been obtained by AvaI/SalI digestion of pACCAR25ΔcrtX, to thereby obtain plasmid pAC-Asta.

TABLE 1

Strains and Plasmids used in the Present Invention

| Strain/Plasmid | Nature* | Reference/Manufacturer |
|---|---|---|
| Strain | | |
| *Brevundimonas* sp. MBIC03018 | 2-Hydroxylated carotenoid-producing bacterium (strain SD-212) | Yokoyama et al, 1996 |
| *Escherichia coli* XL1-Blue MR | Host of cosmid vector SuperCos 1 | Stratagene |
| *E. coli* DH5 α | Host for genetic engineering experiments | TOYOBO |
| Plasmid | | |
| pACCAR16 Δ crtX | Cm$^r$; plasmid comprising crtE, crtB, crtI and crtY | Misawa et al, 1995 |
| pACCAR25 Δ crtX | Cm$^r$; plasmid comprising crtE, crtB, crtI, crtY and crtZ | Misawa et al, 1995 |
| pAC-Cantha | Cm$^r$; plasmid comprising crtE, crtB, crtI, crtY and crtW | Present invention |
| pAC-Asta | Cm$^r$; plasmid comprising crtE, crtB, crtI, crtY, crtZ and crtW | Present invention |
| SuperCos 1 | Ap$^r$; cosmid vector | Stratagene |
| pBluescript II KS- | Ap$^r$; cloning vector | TOYOBO |
| pGEM-T Easy | Ap$^r$; cloning vector | Promega |
| pUC18 | Ap$^r$; cloning vector | TOYOBO |
| pCos5-2 | Ap$^r$; *Brevundimonas* sp. MBIC03018-derived 47 kb DNA fragment (partially digested with Sau3AI) is inserted at the BamHI site of SuperCos 1 | Present invention |
| CRTI-SD212 | Ap$^r$; *Brevundimonas* sp. MBIC03018-derived crtI is PCR amplified and inserted into pGEM-T Easy | Present invention |
| p5Bre2–15 | Ap$^r$; pCos5-2-derived 12 kb EcoRI fragment is inserted into pBluescript II KS- | Present invention |
| pUCBre-011 | Ap$^r$; p5Bre2-15-derived 2-hydroxylase gene is PCR amplified and inserted into pUC18 | Present invention |

Ap$^r$: ampicillin resistance;
Cm$^r$: chloramphenicol resistance

Miura, Y., Kondo, K., Saito, T., Shimada, H., Fraser, P. D., Misawa, "Production of the carotenoids lycopene, β-carotene, and astaxanthin in the food yeast *Candida utilis*" N., Appl. Environ. Microbiol., 64, 1226-1229, 1998

Misawa, N., Nakagawa, M., Kobayashi, K., Yamano, S., Izawa, Y. Nakamura, K., and Harashima, K., "Elucidation of the *Erwinia uredovora* carotenoid biosynthetic pathway by the functional analysis of gene products expressed in *Escherichia coli*", J. Bacteriol., 172, 6704-6712, 1990

Sambrook, J., Fritsch, E. F., and Maniatis T. 1989. "Molecular cloning: a laboratory manual. 2nd ed.", Cold Spring Harbor Laboratory Press, Cold Spring Harbor, N.Y. Yokoyama, A., Miki, W., Izumida, H., Shizuri, Y. 1996. "New Trihydroxy-keto-carotenoids isolated from an astaxanthin-producing marine bacterium", Biosci. Biotechnol. Biochem. 60, 200-203, 1996 (Non-Patent Document 2)

Misawa, N., Satomi, Y., Kondo, K., Yokoyama, A., Kajiwara, S., Saito, T., Ohtani, T., and Miki, W., "Structure and functional analysis of a marine bacterial carotenoid biosynthesis gene cluster and astaxanthin biosynthetic pathway proposed at the gene level", J. Bacteriol. 177, 6575-6585, 1995 (Non-Patent Document 1)

EXAMPLE 2

Genetic Engineering Experiments

Conventional genetic engineering experiments such as construction of plasmids, treatment with restriction enzymes, ligation reaction and transformation were conducted according to the methods disclosed in Sambrook et al. (1989), op. cit.

EXAMPLE 3

Preparation of Chromosomal DNA from *Brevundimonas* sp. Strain SD-212

*Brevundimonas* sp. strain SD-212 (SD212; MBIC 03018) was cultured in 300 ml of Marine Broth (MB) medium (Difco) at 25° C. for 3 days. Cells were harvested, washed with STE buffer (100 mM NaCl, 10 mM Tris-HCl, 1 mM EDTA, pH 8.0) twice, thermally treated at 68° C. for 15 min and then suspended in solution 1 (50 mM glucose, 25 mM Tris-HCl, 10 mM EDTA, pH 8.0) containing 5 mg/ml lysozyme (Sigma) and μg/ml RNase A (Sigma). After 1 hr incubation at 37° C., Protenase K (Sigma) was added thereto to give a concentration of 250 μg/ml, followed by incubation at 37° C. for 10 min. N-Lauroylsarcosin-Na was added thereto to give a final concentration of 1% and mixed gently and thoroughly by inverting, followed by incubation at 37° C. for 3 hr. After several times of phenol/chloroform extraction, while adding two volumes of ethanol slowly, chromosomal DNA deposited was wound around a glass rod and rinsed with 70% ethanol. Then, the DNA was dissolved in 2 ml of TE buffer (10 mM Tris-HCl, 1 mM EDTA, pH 8.0) to prepare a chromosomal DNA solution.

EXAMPLE 4

Amplification of Partial Fragment of Phytoene Desaturase Gene (crtI) by PCR

A partial fragment of phytoene desaturase gene (crtI) was amplified by PCR using crtI-Fo primer (5'-TTY GAY GCI GGI CCI ACI GT -3')(SEQ ID NO: 37) and crtI-Re primer (5'-CCI GGR TGI GTI CCI GCI CC-3')(SEQ ID NO: 38)

(which had been designed utilizing the homology of crtI genes among carotenoid producing bacteria) and the chromosomal DNA from *Brevundimonas* sp. strain SD-212 obtained as described above as a template. As a thermal resistance DNA polymerase, La-Taq (TaKaRa) was used. After thermal denaturation at 96° C. for 5 min, 35 cycles of 98° C. for 20 sec, 58° C. for 30 sec and 72° C. for 1 min were carried out. The amplified products were confirmed by 1% agarose gel electrophoresis. Then, a 1.1 kb DNA fragment was cut out from the gel and purified with Qiagen Gel Extraction kit (QIAGEN) or Gene Clean II Kit (BIO101). The purified DNA fragment was ligated to pGEM-T Easy and transformed into *E. coli* (DH5α). This plasmid was designated pCRTI-SD212. The *E. coli* was cultured in 2 ml of ampicillin-added LB liquid medium at 37° C. overnight, followed by extraction of the plasmid. The nucleotide sequence (partial) of the extracted plasmid was determined using a DNA sequencing kit (Big Dye Terminator Cycle Sequencing Ready Reaction Kit ver.2; Perkin-Elmer) and a model 3700 DNA sequencer (Perkin-Elmer) according to the protocol attached. The thus determined DNA sequence (SEQ ID NO: 1) was subjected to homology search using Blast (Altschul and Lipman, 1990). As a result, it was confirmed that this DNA sequence has a homology to phytoene desaturase gene (crtI). A part of the PCR amplified and purified DNA fragment was used as a probe in the colony hybridization and Southern hybridization conducted in Examples 7 and 8.

Altschul, S. F. and Lipman, D. J., "Protein database search for multiple alignments", Proc. Natl. Acad. Sci. USA 87, 5509-5513, 1990.

EXAMPLE 5

Construction of Cosmid Library

Experimental procedures up to acquisition of phage particles from a prepared solution of *Brevundimonas* sp. strain SD-212 chromosomal DNA were according to the instructions attached to SuperCos 1 Cosmid Vector Kit (Stratagene). Briefly, the chromosomal DNA from *Brevundimonas* sp. strain SD-212 was partially digested with Sau3AI and ligated to the BamHI site of the cosmid vector, followed by packaging into phage particles using LAMBDA INN (Nippon Gene). Subsequently, *E. coli* XL1-Blue MR and pACCAR25ΔcrtX-carrying *E. coli* XL1-Blue MR that produces zeaxanthin were infected with the resultant phage particles. On Ap containing LB plates and Ap+Cm containing LB plates, approx. 1000 Ap resistant colonies and approx. 1000 Ap+Cm resistant colonies were obtained, respectively. The resultant colonies were transferred onto fresh antibiotic containing LB plates with sterilized toothpicks. At this stage, no colonies were obtained which exhibit a color change.

This cosmid vector SuperCos 1 (Stratagene) is a 7.9 kb vector and capable of insertion of a 30-45 kb DNA fragment. This cosmid vector has the following advantages. Since it has two cos regions, efficient packaging is possible. Dephosphorylation operation for preventing the packaging of cosmid concatemers is unnecessary. Since it is possible to dephosphorylate the chromosomal DNA to be inserted, mixing of re-ligated fragments of the chromosomal DNA fragment need not be worried about. Size fractionation is also unnecessary.

EXAMPLE 6

Attempt of Expression Cloning

Using 700 colonies from the cosmid library constructed in Example 5 using the pACCAR25ΔcrtX-carrying and zeaxanthin-producing *E. coli* as a host, a 2 ml aliquot of each colony was cultured. Carotenoid pigments were extracted therefrom with acetone, followed by analysis of the carotenoids with HPLC-PDA (photodiode array detector). The procedures are described in Example 11. Whether novel carotenoid(s) was/ were produced in addition to the control zeaxanthin was examined. As a result, no colonies were obtained that synthesize novel carotenoid(s). Therefore, the inventors concluded that expression cloning of the carotenoid biosynthesis genes of *Brevundimonas* sp. strain SD-212 is impossible.

EXAMPLE 7

Colony Hybridization

Using 500 colonies from the cosmid library constructed in Example 5 using *E. coli* XL1-Blue MR as a host and the partial fragment of phytoene desaturase gene (crtI) amplified in Example 4 by PCR as a probe, colony hybridization was performed to thereby screen for crtI-containing clones. First, the *E. coli* was seeded on plates and cultured at 37° C. At this time, 48 colonies were seeded per plate. After overnight culture, a Hybond-N+membrane 82 mm in diameter (Amersham Pharmacia) was placed on the plate and a mark was put on the membrane an injection needle. The membrane was peeled off and placed with the surface which cells adhered onto upward. The membrane was incubated for 5 min with a 3 mm filter paper (Whatman) containing 10% SDS solution and incubated for another 5 min with a 3 mm filter paper containing a denaturing solution (1.5 M NaCl, 0.5 M NaOH). Then, the membrane was dipped in a neutralizing solution (1.5 M NaCl, 0.5M Tris-HCl) for 5 min (twice). Further, the membrane was washed with 2×SSC twice. At this time, the membrane was wiped off strongly with Kimtowel so that no cell debris remained on the membrane. After these treatments, the membrane was air-dried on Kimtowel and Kimwipe for 30 min and baked at 80° C. for 2 hr to thereby immobilize DNA on the membrane. A DNA probe was prepared using Alkphos Direct Labeling and Detection System (Amersham Pharmacia) according to the manufacturer's protocol and used in colony hybridization. As a result of this colony hybridization using the partial fragment of phytoene desaturase gene (crtI) as a probe DNA, 6 positive clones were obtained from the 500 colonies used. The plasmids contained in these 6 clones were designated pCos5-1, pCos5-2, pCos7-1, pCos8-1, pCos9-1 and pCos10-1, respectively.

EXAMPLE 8

Southern Hybridization

Figure 3:
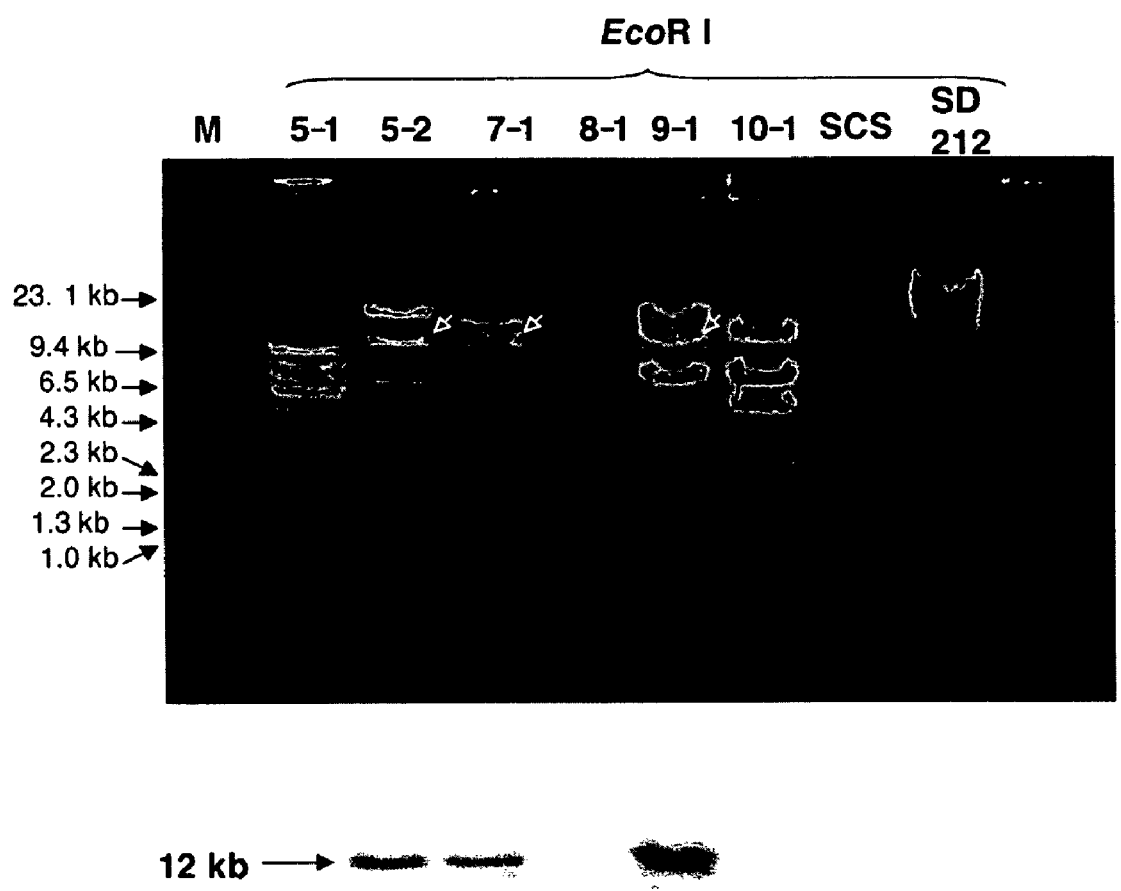
FIG. 3 shows the results of Southern hybridization (EcoRI digestion) using a crtI fragment as a probe [M: size marker (λ/HindIII-φX174/HaeIII digest); lanes 5-1 to 10-1: cosmid clones; SCS: cosmid vector SuperCosI; SD212: SD-212 chromosomal DNA]

The 6 positive clones selected in Example 7 were cultured in 2 ml of Ap-added LB liquid medium at 37° C. overnight, followed by extraction of plasmid DNA. The extracted plasmid DNA was completely digested with EcoRI by incubating at 37° C. for several hours and then electrophoresed. As controls, vector SuperCos 1 and similarly digested *Brevundimonas* sp. strain SD-212 chromosomal DNA were used. Electrophoresis was performed in a small submarine-type electrophoresis bath Mupid (Cosmobio) using 1% agarose gel at 50 V for about 70 min. As an electrophoresis buffer, 1×TBE buffer was used. After the electrophoresis, the gel was stained with ethidium bromide and decolored with ultra-pure water. Then, photographs were taken under UV radiation (FIG. 3). Subsequently, the DNA was transferred onto a nylon membrane (Hybond N+) by capillary blotting with 0.4M NaOH solution. After this treatment, the membrane was baked at 80°

Figure 4:
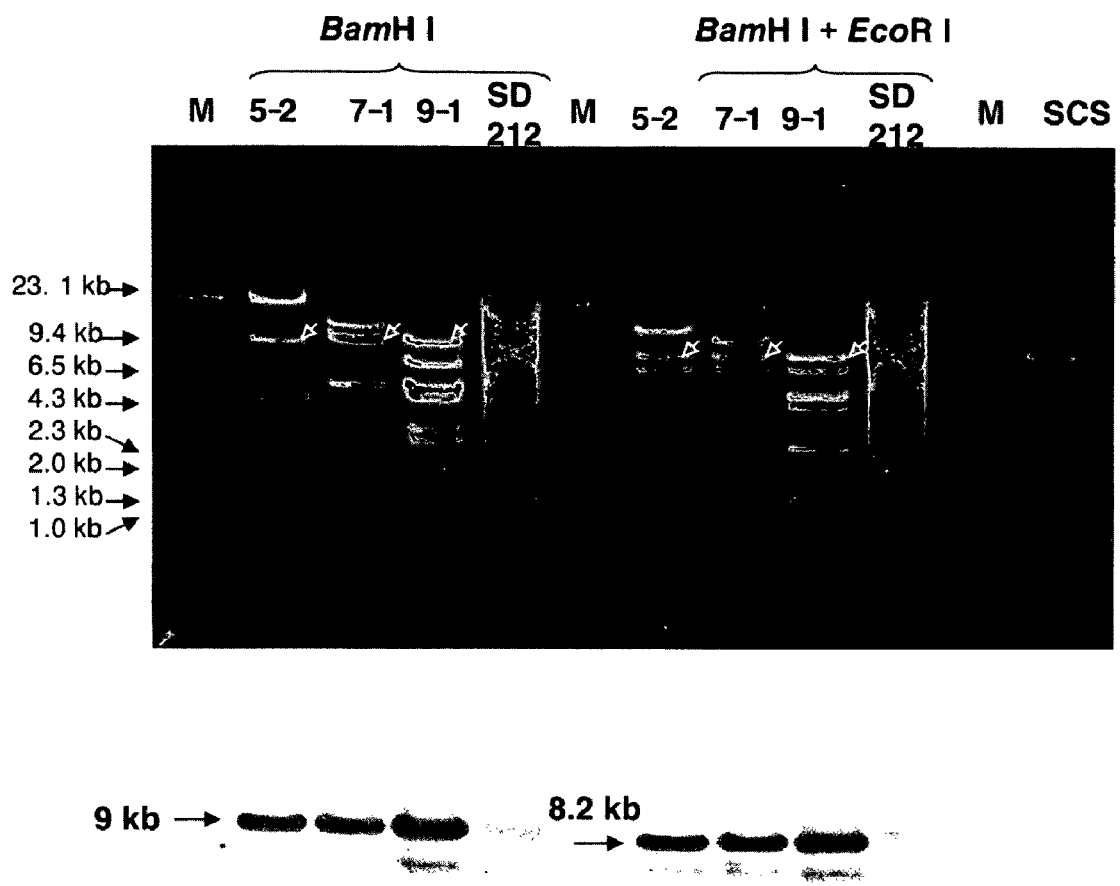
FIG. 4 shows the results of Southern hybridization (BamHI and BamHI/EcoRI digestion) using a crtI fragment as a probe [M: size marker (λ/HindIII-φX174/HaeIII digest); lanes 5-2 to 9-1: cosmid clones; SD212: SD-212 chromosomal DNA; SCS: BamHI/EcoRI digest of cosmid vector SuperCos I].

C. for 2 hr to thereby immobilize the DNA on the membrane. Subsequently, Southern hybridization was performed using Alkphos Direct Labeling and Detection System (Amersham Pharmacia) according to the protocol attached to the kit. As a probe DNA, the above-described partial fragment of phytoene desaturase gene (crtI) was used. As a result, 3 clones (pCos5-2, pCos7-1 and pCos9-1) out of the 6 positive clones showed a 12 kb EcoRI fragment-positive signal (FIG. 3). The control SD-212 chromosomal DNA exhibited a smear band on the high molecular side as a result of the electrophoresis; this DNA was little digested. Although slightly, a positive signal was recognized on the high molecular side. One of the reasons for this little digestion may be that the chromosomal DNA had been partially methylated and this inhibited the degradation by EcoRI. Further, a similar experiment was conducted in which the plasmids of the 3 positive clones, SuperCos 1, and the chromosomal DNA from *Brevundimonas* sp. strain SD-212 were digested with BamHI or BamHI-EcoRI (FIG. 4). The results revealed that a 9 kb DNA fragment-positive signal was recognized when digested with BamHI, and a 8.2 kb DNA fragment-positive signal was recognized when digested with BamHI-EcoRI. Although weak, positive signals were also recognized at the same positions in the chromosomal DNA from *Brevundimonas* sp. strain SD-212.

EXAMPLE 9

Analysis of a Carotenoid Gene Cluster

Figure 5:
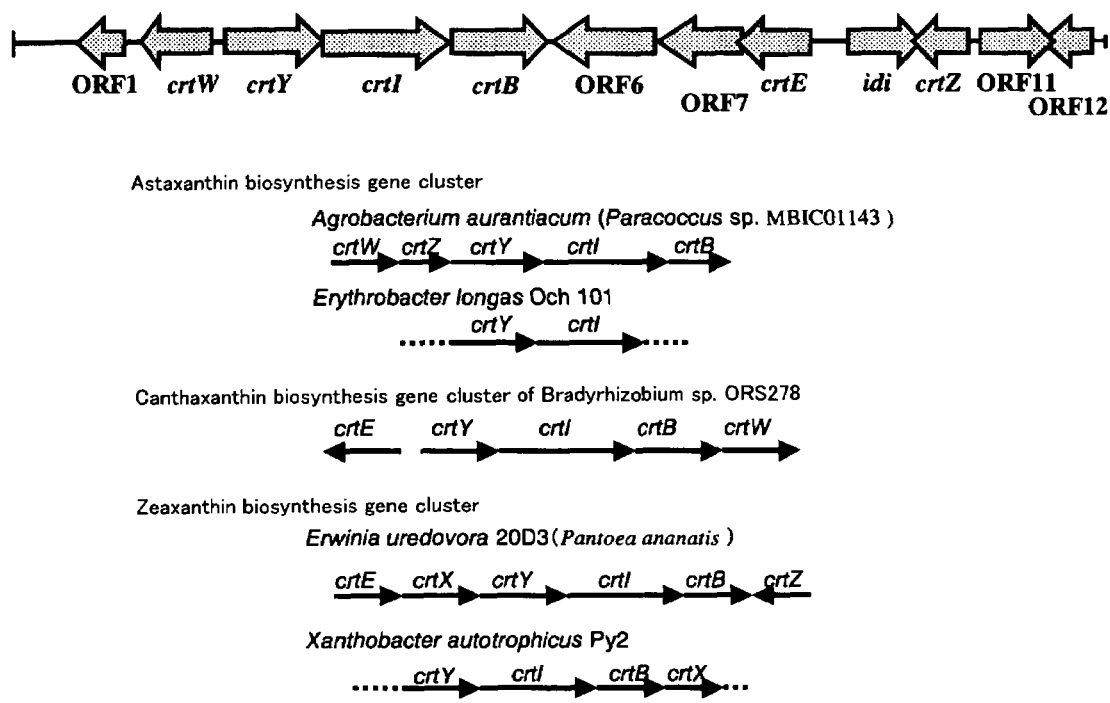
FIG. 5 shows the structure of the carotenoid biosynthesis gene cluster (12 kb EcoRI fragment) of *Brevundimonas* sp. strain SD-212.

Of the 3 positive clones selected in Example 8 (pCos5-2, pCos7-1 and pCos9-1), pCos5-2 was used in this experiment. The 12 kb insert was cut out with EcoRI, ligated to the EcoRI site of plasmid vector pBluescript II KS-, and transformed into *E. coli* DH5α. This plasmid was designated p5Bre2-15. The resultant *E. coli* was cultured in 2 ml of Ap-added LB liquid medium at 37° C. overnight, followed by extraction of plasmid. The nucleotide sequence of the extracted plasmid was sequenced using Big Dye Terminator Cycle Sequencing Ready Reaction Kit ver. 2 (Perkin-Elmer) and model 3700 DNA sequencer (Perkin-Elmer) according to the manufacturer's protocol. Gene-coding regions of the thus determined DNA sequence (SEQ ID NO: 2) were estimated using GeneMark.hmm (Lukashin A. and Borodovsky M.) and SD-like sequences were confirmed. As a result, 12 open reading frames (ORFs) were found in the 12 kb fragment (FIG. 5). Individual ORFs were subjected to homology search at the amino acid level using Blast. The results revealed that 7 ORFs out of 12 show homology to existing carotenoid biosynthesis genes (crtW, crtY, crtI, crtB, crtE, crtZ and idi) (Table 2). The remaining 5 genes (ORFs) were unknown genes having no overall homology to any existing gene. The search of identity (the ratio of identical amino acid sequence) between the *Brevundimonas* sp. strain SD-212-derived 7 Crt enzymes (including one Idi) showing homology to known carotenoid biosynthesis enzymes and other organism-derived corresponding enzymes was performed as described below to ensure accuracy. Briefly, using Blast program (ver. 2) (Altschul, S. F., Madden, T. L., Schaffer, A. A., Zhang, J., Zhang, Z., Miller, W., and Lipmann, D. J., *Nucleic Acids Res.* 25, 3389-3402, 1997), homology search was carried out through GenBank/DDBJ databases. Subsequently, using the hit amino acid sequences, individual Crt proteins were analyzed with Clustal W program (ver. 1.8) (Higgins, D. G., Thompson, J. D., and Gibson, T. J., *Methods Enzymol.* 266, 383-402, 1996) and GeneDoc program (Nicholas, K. B., Nicholas H. B. Jr., and Deerfield, D. W. II., *Embnew. News* 4, 14, 1997) to thereby determine the identity between entire regions. Table 2 shows the identities between individual *Brevundimonas* sp. strain SD-212-derived 7 Crt enzymes (including one Idi) and other bacterium-derived Crt proteins that showed the highest homology thereto. The results of this analysis revealed that the *Brevundimonas* sp. strain SD-212-derived 7 Crt enzymes (including one Idi) show only moderate or low homology to known, other organism-derived corresponding proteins. As seen from Table 2, even in the SD-212-derived CrtI which showed the highest homology, the identity was 72%. More surprisingly, the SD-212-derived CrtZ and CrtE have no known, other organism-derived corresponding proteins showing more than 50% identity. Even at the highest, the identities were 46% and 39%, respectively. The crtZ gene of SD-212 is encoded by the nucleotides from positions 1319 to 1804 of the complementary strand of the 12 kb EcoRI fragment (11,991 kb) as shown in SEQ ID NO: 2. The nucleotide sequence of this crtZ gene is shown in SEQ ID NO: 29, and the amino acid sequence encoded thereby (CrtZ) is shown in SEQ ID NO: 30. The crtE gene of SD-212 is encoded by the nucleotides from positions 2963 to 3859 of the complementary strand of the 12 kb EcoRI fragment (11,991 kb) as shown in SEQ ID NO: 2. The nucleotide sequence of this crtE gene is shown in SEQ ID NO: 31, and the amino acid sequence encoded thereby (CrtE) is shown in SEQ ID NO: 32. Further, examination of the locations of individual crt genes (i.e., locations of crtW and crtZ, orientations of other genes, etc.) revealed that the carotenoid biosynthesis gene cluster from SD-212 is greatly different in structure from the previously reported carotenoid biosynthesis gene clusters of bacteria producing carotenoids with hydroxylated β-ionone ring(s) (Misawa et al., 1990 & 1995; Hannibal et al., 2000) (FIG. 5). An IPP isomerism gene (idi) present within a carotenoid biosynthesis gene cluster was found for the first time. By the way, *E. coli* carrying plasmid p5Bre2-15 containing all of the above-described 12 ORFs (including 7 crt genes) was unable to produce any carotenoid. Therefore, it has become clear that the carotenoid biosynthesis gene cluster of *Brevundimonas* sp. strain SD-212 is not capable of functional expression as it is.

TABLE 2

Characteristics and Predicted Functions of the Various ORFs Present in the Carotenoid Biosynthesis Gene Cluster in *Brevundimonas* sp. Strain SD-212

| Designation of ORF | GC % | No. of Amino Acid Residues | Predicted Function | Homology to Gene Product of Other Organism (%) | | GenBank number |
|---|---|---|---|---|---|---|
| ORFI | 69.7 | 140 | Unknown | | | |
| crtW | 69.6 | 244 | β-carotene C4 oxygenase | CrtW: *Brevundimonas aurantiaca* | (96%) | AAN86030 |
| crtY | 70.2 | 392 | lycopene cyclase | CrtY: *Xanthobacter autotrophicus* Py2 | (52%) | AF408848 |

TABLE 2-continued

Characteristics and Predicted Functions of the Various ORFs Present in the
Carotenoid Biosynthesis Gene Cluster in Brevundimonas sp. Strain SD-212

| Designation of ORF | GC % | No. of Amino Acid Residues | Predicted Function | Homology to Gene Product of Other Organism (%) | | GenBank number |
|---|---|---|---|---|---|---|
| crtI | 67.3 | 493 | phytoene desaturase | CrtI: *Xanthobacter autotrophicus* Py2 | (72%) | AF408848 |
| crtB | 72 | 310 | phytoene synthase | CrIB: *Xanthobacter autotrophicus* Py2 | (53%) | AF408848 |
| ORF6 | 75.8 | 354 | Unknown | | | |
| ORF7 | 74.6 | 315 | Unknown | | | |
| crtE | 71 | 298 | GGPP synthase | CrtE: *Xanthobacter autotrophicus* Py2 | (39%) | AF408847 |
| idi | 74.9 | 350 | Type II IPP isomerase | IPP isomerase: *Pantoea agglomerans* | (53%) | M87280 |
| crtZ | 66.9 | 161 | β-carotene C3 hydroxylase | CrtZ: *Pantoea agglomerans* | (46%) | M87280 |
| ORF11 | 70.7 | 257 | Unknown | | | |
| ORF12 | 66.7 | 122 | Unknown | | | |

CrtW, *Brevundimonas aurantiaca* (GenBank number AAN86030);
CrtY, CrtI, CrtB, CrtE, *Xanthobacter* sp. Py2 (GenBank no. AF408848, AF408847);
IPP isomerase(Idi),
CrtZ, *Pantoea agglomerans* (Erwinia herbicola Eho10) (GenBank no.M87280)

Lukashin A. and Borodovsky M., 1998, "GeneMark.hmm: new solutions for gene finding", NAR, Vol. 26, No. 4, pp.1107-1115.

Misawa, N., Nakagawa, M., Kobayashi, K., Yamano, S., Izawa, Y., Nakamura, K. and Harashima, K., "Elucidation of the *Erwinia uredovora* carotenoid biosynthetic pathway by functional analysis of gene products expressed in *Escherichia coli*. J. Bacteriol. 172, 6704-6712, 1990

Misawa, N., Satomi, Y., Kondo, K., Yokoyama, A., Kajiwara, S., Saito, T., Ohtani, T., and Miki, W., "Structure and functional analysis of a marine bacterial carotenoid biosynthesis gene cluster and astaxanthin biosynthetic pathway proposed at the gene level", J. Bacteriol. 177, 6575-6585, 1995 (Non-Patent Document 1)

Hannibal, L., Lorquin, J., D'Ortoli, N. A., Garcia, N., Chaintreuil, C., Masson-Boivin, C., Dreyfus, B. and Giraud, E., "Isolation and characterization of canthaxanthin biosynthesis genes from the photosynthetic bacterium Bradyrhizobium sp. strain ORS278", J. Bacteriol. 182, 3850-3853, 2000

Larsen, R. A., Wilson, M. M., Guss, A. M. and Metcalf, W. W., "Genetic analysis of pigment biosynthesis in Xanthobacter autotrophicus Py2 using a new, highly efficient transposon mutagenesis system that is functional in a wide variety of bacteria", Arch. Microbiol. 178, 193-201, 2002

EXAMPLE 10

Construction of β-Galactosidase Fusion Protein Expression Plasmids

In order to elucidate the functions of the ORFs, each ROF was amplified by PCR using the DNA of plasmid p5Bre2-15 as a template so that each ORF is expressed as a fusion protein with the lead sequence of β-galactosidase gene (lacZ) encoded by an *E. coli* vector pUC18 (TOYOBO). Thus, individual plasmids for expressing β-galactosidase fusion proteins were constructed. The inventors expected that each ORF would be functionally expressed in *E. coli* by this method. Specifically, individual ORFs were amplified with primers (as shown in SEQ ID NOS: 5-28) designed so that amplified products with 5' terminal EcoRI site and 3' terminal BamHI or XbaI site could be obtained. As a thermal resistance DNA polymerase, La-Taq (TaKaRa) was used. After thermal denaturation at 96° C. for 5 min, 35 cycles of 98° C. for 20 sec, 56° C. for 30 sec and 72° C. for 1 min were carried out. A part of the amplified products was confirmed by 1% agarose gel electrophoresis. The remaining amplified product was ethanol-precipitated, digested with EcoRI+BamHI or Eco RI +XbaI, and then confirmed by 1% agarose gel electrophoresis. Subsequently, the DNA fragment with an expected length was cut out from the gel and purified with Qiagen Gel Extraction kit (QIAGEN) or Gene Clean II Kit (BIO101). The purified DNA was ligated to the EcoRI-BamHI or EcoRI-XbaI site of pUC18, and transformed into *E. coli* DH5α. These β-galactosidase fusion protein expression plasmids are designed so that a leader sequence of β-galactosidase consisting of 7 amino acids (Met Thr Met Ile Thr Asn Ser) is added before the inherent starting amino acid Met of each ORF.

EXAMPLE 11

Expression of β-galactosidase—Individual Crt Fusion Protein Genes and Analysis of Pigment Production

Figure 2:
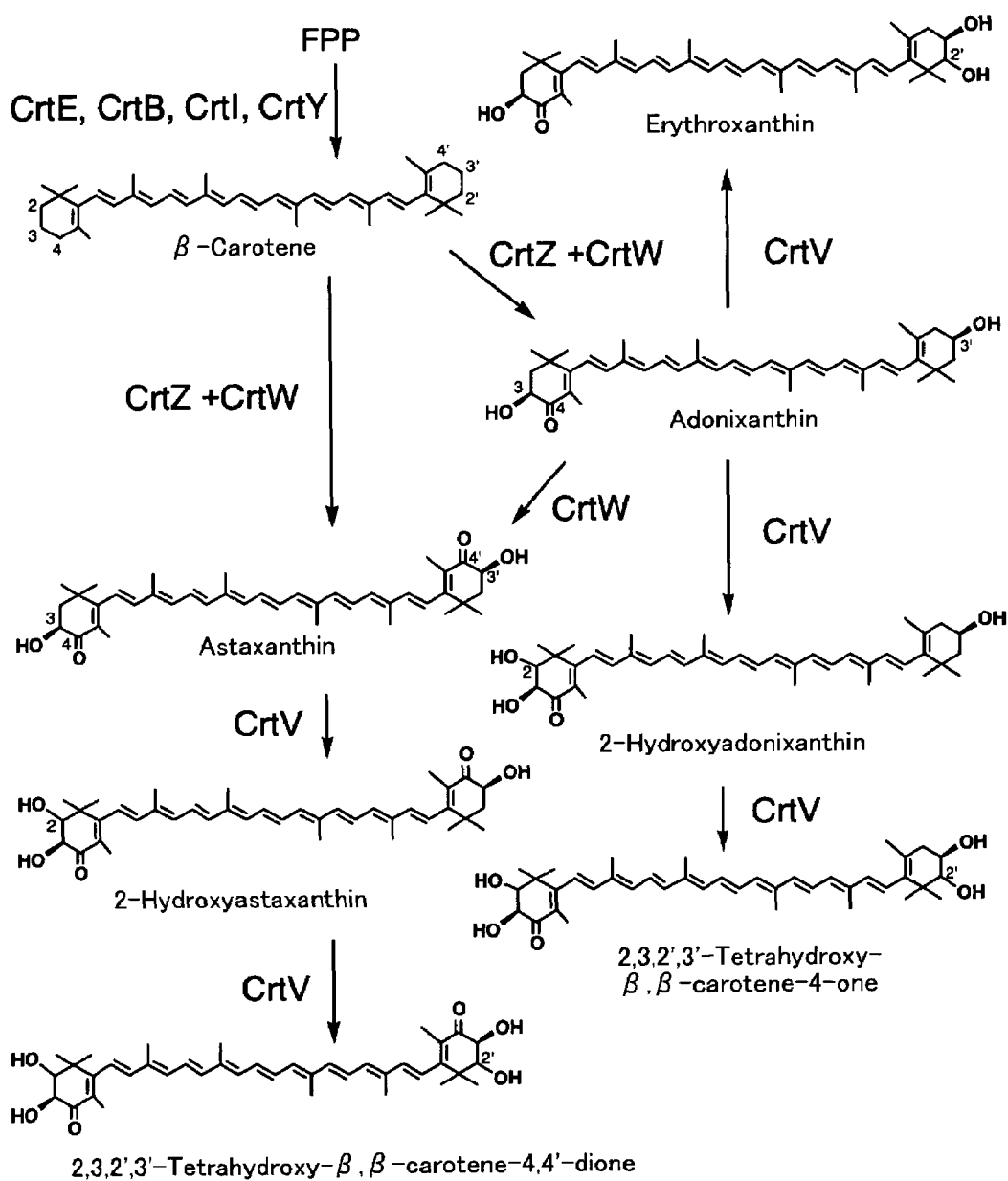
FIG. 2 is a diagram showing the carotenoids produced by *Brevundimonas* sp. strain SD-212 and an estimated synthesis pathway for those carotenoids.

*E. coli* clones carrying plasmids containing crtE, crtB, crtI, crtY, crtZ and crtW genes, respectively, out of the plasmids described in Example 10 were individually cultured in 2 ml of Ap-added LB liquid medium at 37° C. overnight, followed by extraction of plasmid. The nucleotide sequence of the extracted plasmid was confirmed using Big Dye Terminator Cycle Sequencing Ready Reaction Kit ver. 2 (Perkin-Elmer) and model 3700 DNA sequencer (Perkin-Elmer) according to the manufacturer's protocol. The individual plasmids were designated pUCBre-E (lacZ::crtE), pUCBre-B (lacZ::crtB), pUCBre-I (lacZ::crtI), pUCBre-Y (lacZ::crtY), pUCBre-Z (lacZ::crtZ) and pUCBre-W (lacZ::crtW). Subsequently, these plasmids were introduced into *E. coli* clones carrying the various carotenoid producing plasmids (chloramphenicol (Cm) resistant) indicated at the left side in Table 3. Each of the resultant *E. coli* transformants was cultured in 2 ml of Ap and Cm-added LB liquid medium under induction by addition of 1 mM IPTG at 30° C. for 48 hr. Then, cells were harvested by centrifugation and washed with STE twice. Acetone (200 μl) was added thereto and vortexed to thereby transfer pigments from cells to acetone. The resultant mixture was centrifuged. The supernatant was filtered and subjected to pigment analysis with an HPLC-PDA system (Waters Alliance 2695 and 2996 photodiode array detector). Using a TSK gel ODS-80Ts column (Tosoh), solvents were fed as described below. Solvent A (95% methanol) and solvent B [methanol: tetrahydrofuran (THF)=7:3]) were used. First, solvent A 100% was fed for 5 min, followed by a linear gradient from solvent A to solvent B for 5 min, and finally solvent B was fed for 8 min. Pigments were detected with a photodiode array detector and analyzed with an accessory software Empower. As standards, pigments extracted from the various carotenoid synthesizing *E. coli* clones (left side, Table 3) or synthesized products were used. By comparing retention times at 470 nm and absorption waveforms, it was confirmed various carotenoids were produced exactly as predicted (right side, Table 3). These results revealed clearly that *Brevundimonas* sp. strain SD-212-derived various fusion crt genes work in *E. coli* and have similar functions to those of the existing crt genes (crtE, crtB, crtI, crtY, crtZ and crtW). However, the expression of pUCBre-I (lacZ::crtI) と pUCBre-Y (lacZ::crtY) was considerably weak in *E. coli*. With respect to SD-212-derived CrtE and CrtZ which show only a 50% or less identity with known, other organism-derived Crt protein, it was confirmed by this experiment that they have strong catalytic activities in *E. coli*. It has become clear that this CrtE has the same catalytic activity as that of *Erwinia uredovora* (*Pantoea ananatis*)-derived CrtE. That is, this CrtE is a GGPP synthase generating geranylgeranyl pyrophosphate (GGPP) from farnesyl pyrophosphate (FPP). It has also become clear that the CrtZ is a β-ionone ring-3-hydroxylase (β-C3-hydroxylase; 3,3'-β-hydroxylase) which has an activity to generate zeaxanthin from β-carotene and to generate astaxanthin from canthaxanthin. FIG. 2 shows the carotenoids produced by *Brevundimonas* sp. strain SD-212. It is evident that SD-212-derived CrtZ is involved in the synthesis of all the carotenoids shown in FIG. 2 in which position 3 of the β-ionone ring is hydroxylated (e.g., 2-hydroxyastaxanthin and 2-hydroxyadonixanthin).

producing plasmids (Cm resistant) indicated at the left side in Table 3. Each of the resultant *E. coli* transformants was cultured in 2 ml of Ap and Cm-added LB liquid medium under induction by addition of 1 mM IPTG at 30° C. for 48 hr. Then, cells were harvested by centrifugation and washed with STE twice. Acetone (200 μl) was added thereto and vortexed to thereby transfer pigments from cells to acetone. The resultant mixture was centrifuged. The supernatant was filtered and subjected to pigment analysis with an HPLC-PDA system in the same manner as described in Example 11.

Figure 6:
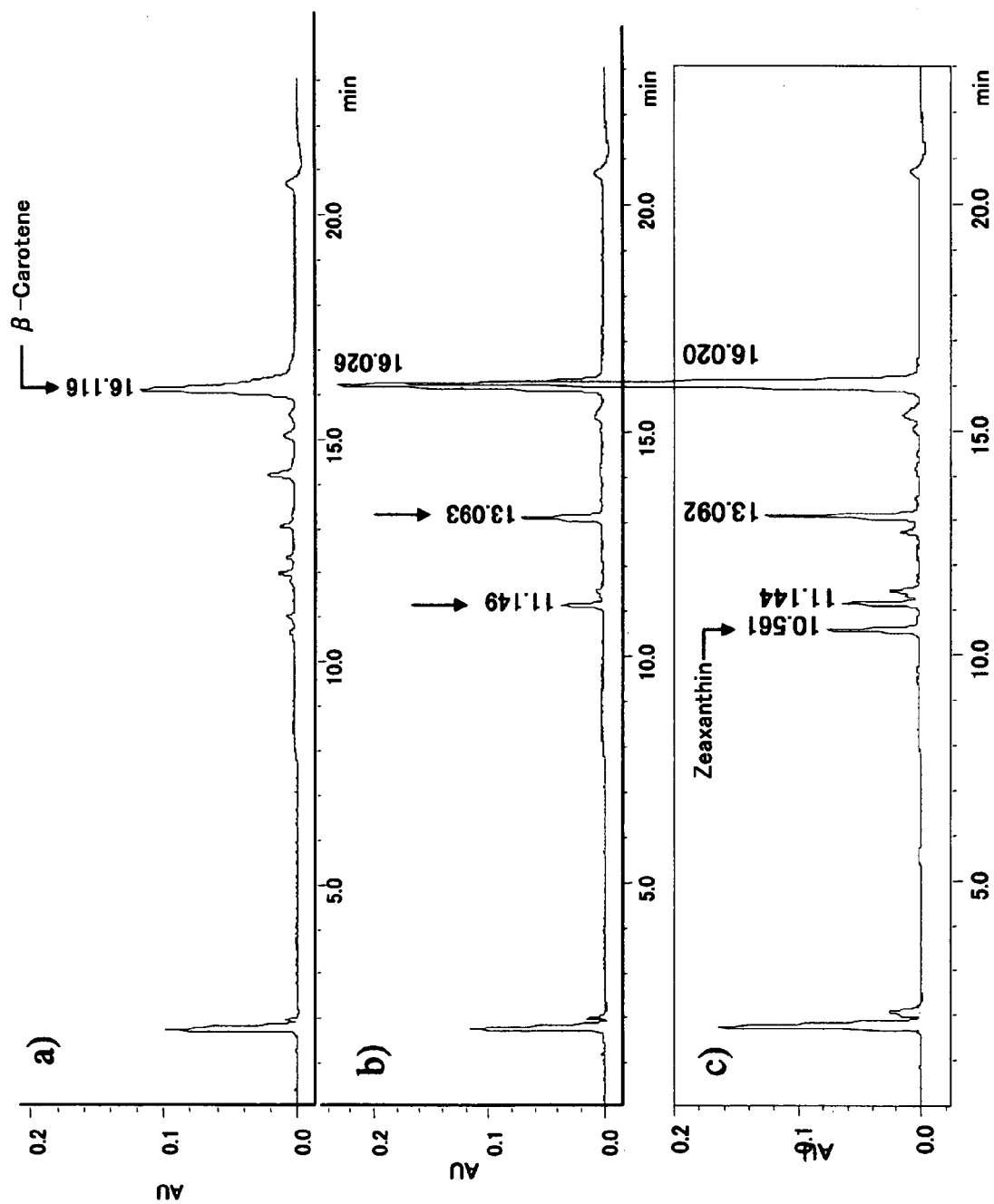
FIG. 6 shows the results of HPLC-PDA analysis using pACCAR16ΔcrtX (plasmid for β-carotene production)-introduced *E. coli* as a host. a) HPLC chromatogram of pigments produced by pACCAR16ΔcrtX-introduced *E. coli* (470 mn). b) HPLC chromatogram of pigments produced by pUCBre-O11 and pACCAR16ΔcrtX-introduced *E. coli* (470 mn). The peaks of novel pigments are marked with arrows. c) HPLC chromatogram when zeaxanthin was added to b) above (470 nm).

As a result of the above experiment, plasmid pUCBre-O11-introduced *E. coli* alone produced a positive result (the nucleotide sequence of ORF11 is shown in SEQ ID NO: 3, and the amino acid sequence encoded thereby is shown in SEQ ID NO: 4). Briefly, in the clone which was obtained by introducing the ORF11 fusion protein expression plasmid pUCBre-O11 (lacZ::SD212-ORF11) into pACCARI6ΔcrtX-carrying, β-carotene-producing *E. coli* (DH5α), the resultant pigment extract exhibited the presence of β-carotene (451 nm, 478 nm) at retention time 16 min, the presence of a substance with absorption maximums (451.0 nm, 478.8 nm) at retention time 11 min on the higher polar side, and the presence of a substance with absorption maximums (452.2 nm, 477.6 nm) at retention time 13 min (FIG. 6; marked with arrows). However, the amounts of these conversion products were small. Since these substances may be zeaxanthin, co-HPLC was conducted by mixing the pigment extract solution with an acetone extract whose major component is pACCRT25ΔcrtX-derived zeaxanthin. The results revealed that the two peaks of these conversion products do not overlap

TABLE 3

Identification of the Functions of Various crt Genes from *Brevundimonas* sp. Strain SD-212

| Property of the recombinant *E. coli* used as a host | | Plasmid SD-212-derived crt gene | Identification of carotenoid pigments produced by double-recombinant *E. coil* |
|---|---|---|---|
| Plasmid | Carotenoid to be accumulated | (lacZ ::each crt) | Produced carotenoid |
| pACCAR25 Δ crtE (crtB,I,Y,Z,X) | FPP | pUCBre-E (lacZ ::crtE) | Zeaxanthin, its glucosides |
| pACCAR25 Δ crtB (crtE,I,Y,Z,X) | GGPP | pUCBre-B (lacZ ::crtB) | Zeaxanthin, its glucosides |
| pACCRT-EB (crtE,B) | Phytoene | pUCBre-I (lacZ ::crtI) | Lycopene (in trace amount) |
| pACCRT-EIB (crtE,B,I) | Lycopene | pUCBre-Y (lacZ ::crtY) | γ-Carotene (in trace amount) |
| pACCAR16 Δ crtX (crtE,B,I,Y) | β-carotene | pUCBre-Z (lacZ ::crtZ) | Zeaxanthin(80%), β-Cryptoxanthin(10%) |
| pAC-Cantha (crtE,B,I,Y,W) | Canthaxanthin | pUCBre-Z (lacZ ::crtZ) | Astaxanthin(41%), Adonixanthin(47%) |
| pACCAR16 Δ crtX (crtE,B,I,Y) | β-carotene | pUCBre-W (lacZ ::crtW) | Canthaxanthin(90%), Echinenone(5%) |

EXAMPLE 12

Expression of β-Galactosidase—ORF11 Fusion Protein and Analysis of Pigment Production

Figure 10:
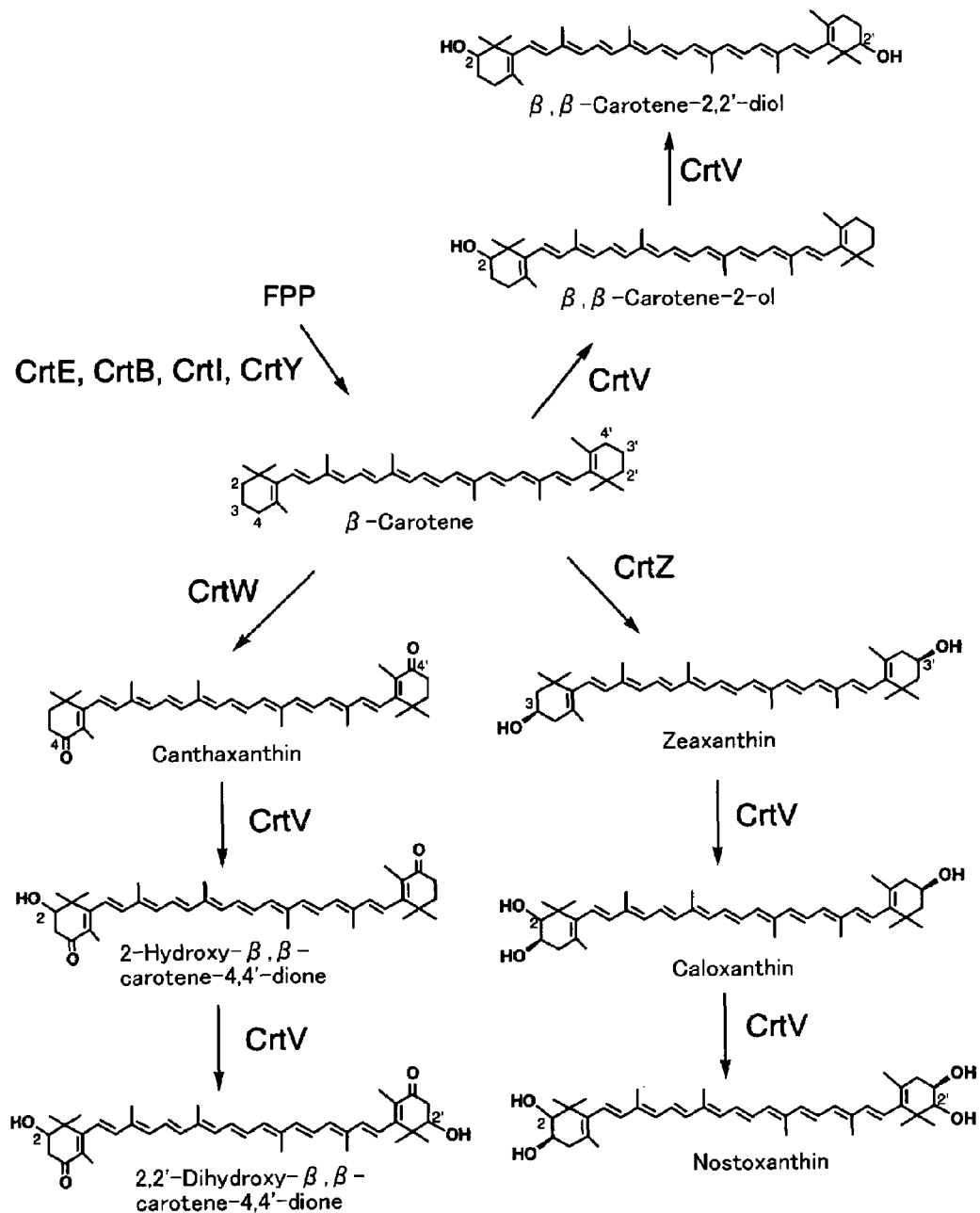
FIG. 10 is a diagram showing carotenoids produced by a recombinant *E. coli* and estimated synthesis pathways for them.

*E. coli* clones carrying plasmids containing ORF1, ORF6, ORF7, ORF11 and ORF12, respectively, out of the plasmids described in Example 10 were individually cultured in 2 ml of Ap-added LB liquid medium at 37° C. overnight, followed by extraction of plasmid. The nucleotide sequence of the extracted plasmid was confirmed using Big Dye Terminator Cycle Sequencing Ready Reaction Kit ver. 2 (Perkin-Elmer) and model 3700 DNA sequencer (Perkin-Elmer) according to the manufacturer's protocol. The individual plasmids were designated pUCBre-O1 (lacZ::SD212-ORF1), pUCBre-06 (lacZ::SD212-ORF6), pUCBre-07 (lacZ::SD212-ORF7), pUCBre-O11 (lacZ::SD212-ORF11) and pUCBre-O12 (lacZ::SD212-ORF12). Subsequently, these plasmids were introduced into *E. coli* clones carrying the various carotenoid with the peak of zeaxanthin (retention time: 10.6 min) (FIG. 6*c*) and thus they are substances different from zeaxanthin. The two carotenoids at retention times of 11 min and 13 min were identified as β,β-carotene-2,2'-diol (β,β-carotene-2,2'-diol; 2,2'-dihydroxy-β-carotene) and β,β-carotene-2-ol (β,β-caroten-2-ol; 2-hydroxy-β-carotene), respectively (see FIG. 10).

Figure 7:
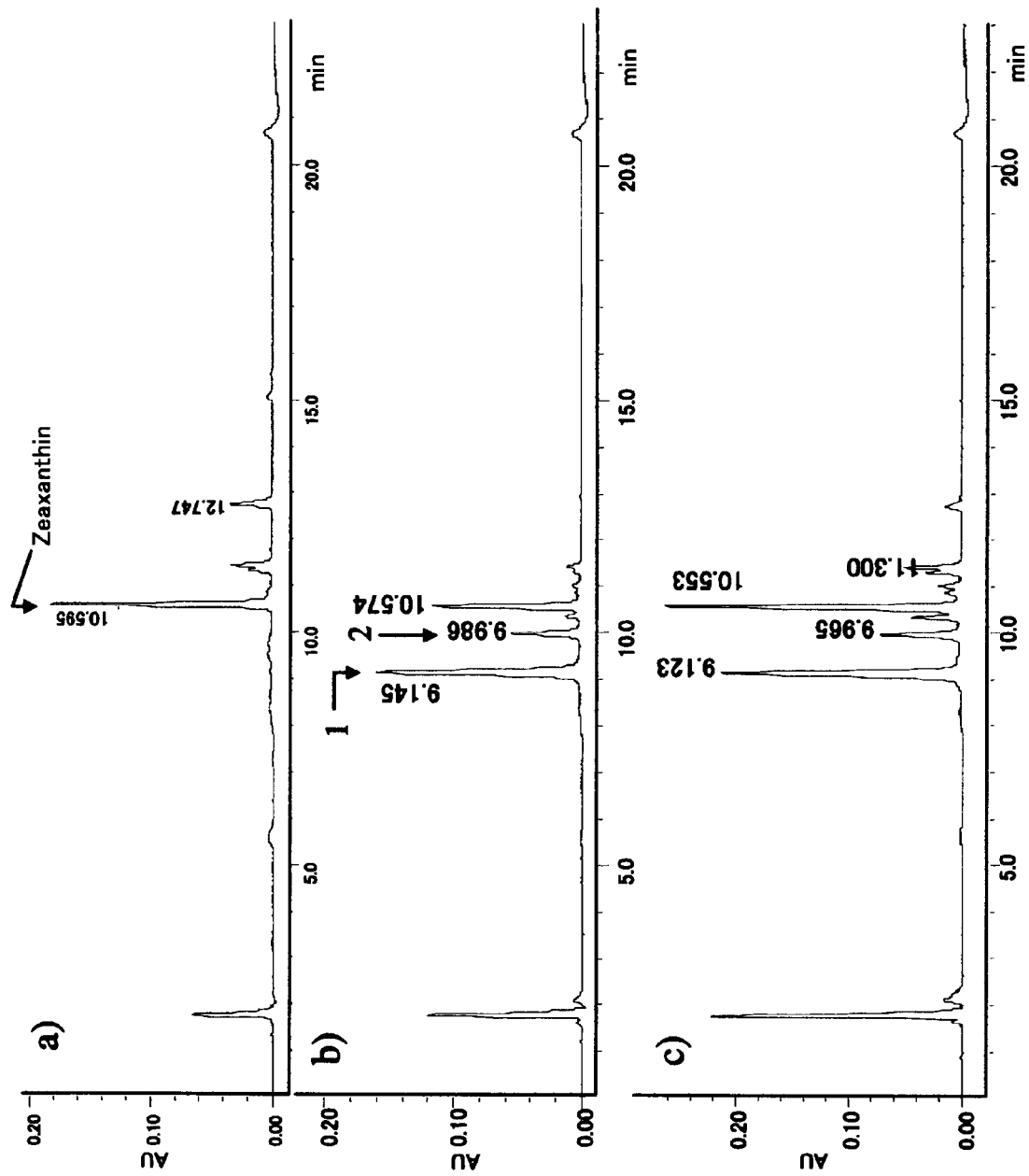
FIG. 7 shows the results of HPLC-PDA analysis using pACCAR25ΔcrtX (plasmid for zeaxanthin production)-introduced *E. coli* as a host. a) HPLC chromatogram of pigments produced by pACCAR25ΔcrtX-introduced *E. coli* (470 mn). b) HPLC chromatogram of pigments produced by pUCBre-O11 and pACCAR25ΔcrtX-introduced *E. coli* (470 mn). The peaks of novel pigments are marked with arrows. c) HPLC chromatogram when zeaxanthin was added to b) above (470 nm). Peaks 1 and 2 were identified as nostoxanthin and caloxanthin, respectively.

In the clone which was obtained by introducing the ORF11 fusion protein expression plasmid pUCBre-O11 (lacZ:: SD212-ORFI 1) into pACCAR25ΔcrtX-carrying, zeaxanthin-producing *E. coli* (DH5α), the resultant pigment extract exhibited the presence of zeaxanthin (451 nm, 480 nm) at retention time 10.6 min. Other new peaks were also observed; substance 1 with absorption maximum (451.0 nm, 478.8 nm) at retention time 9.1 min and substance 2 with absorption maximums (452.2 nm, 477.6 nm) at retention time 9.9 min (FIG. 7; marked with arrows). Carotenoids 1 and 2 were identified as nostoxanthin (2,2'-dihydroxyzeaxanthin) and caloxanthin (2-hydroxyzeaxanthin), respectively (see FIG.

10 and Example 13). The above results demonstrate that the gene product encoded by ORF11 is a β-ionone ring-2-hydroxylase (β-C2-hydroxylase; 2,2'-β-hydroxylase) which is an enzyme capable of introducing a hydroxyl group at the position 2 carbon of the β-ionone ring in carotenoids such as β-carotene and zeaxanthin.

Figure 8:
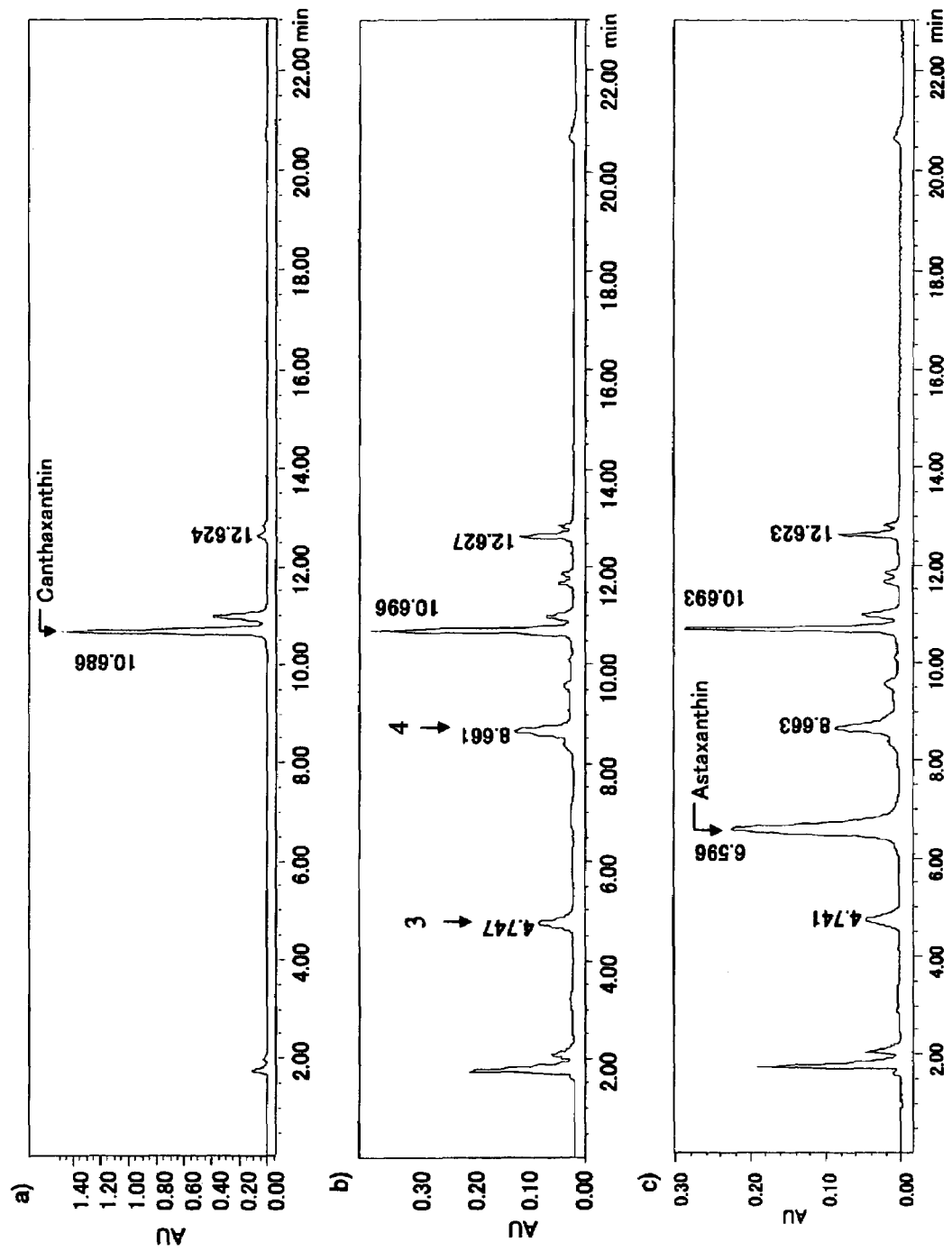
FIG. 8 shows the results of HPLC-PDA analysis using pAC-Cantha (plasmid for canthaxanthin production)-introduced *E. coli* as a host. a) HPLC chromatogram of pigments produced by pAC-Cantha-introduced *E. coli* (470 mn). b) HPLC chromatogram of pigments produced by pUCBre-O11 and pAC-Cantha-introduced *E. coli* (470 nm). The peaks of novel pigments are marked with arrows. c) HPLC chromatogram when astaxanthin was added to b) above (470 nm). Peaks 3 and 4 were identified as 2,2'-dihydroxy-β,β-carotene-4,4'-dione and 2-hydroxy-β,β-carotene-4,4'-dione, respectively.

Subsequently, plasmid pUCBre-011 was introduced into canthaxanthin-producing *E. coli* (DH5α) which carries plasmid pAC-Cantha containing the gene of an enzyme introducing a keto group at position 4 of β-ionone ring, and the resultant pigments were analyzed in the same manner as described in Example 11. As a result, a peak of canthaxanthin was recognized at retention time 10.7 min. Besides, there were recognized on the higher polar side a peak of substance 3 at retention time 4.7 min and a peak of substance 4 at retention time 8.7 min (FIG. 8; marked with arrows). The maximum absorption wavelengths were 478 nm and 474 nm, respectively. These waveforms suggested the presence of substances showing a single-mountain form typical in those carotenoids having keto group(s) in the conjugated system of the β-ionone ring. Further, the results of co-HPLC with astaxanthin (retention time: approx. 6.6 min) confirmed that these peaks are not astaxanthin (FIG. 8*c*). Carotenoids 3 and 4 were identified as 2,2'-dihydroxy-β,β-carotene-4,4'-dione (2,2'-dihyrroxycanthaxanthin) and 2-hydroxy-β,β-carotene-4,4'-dione (2-hydroxcanthaxanthin) (see FIG. 10 and Example 13).

Figure 9:
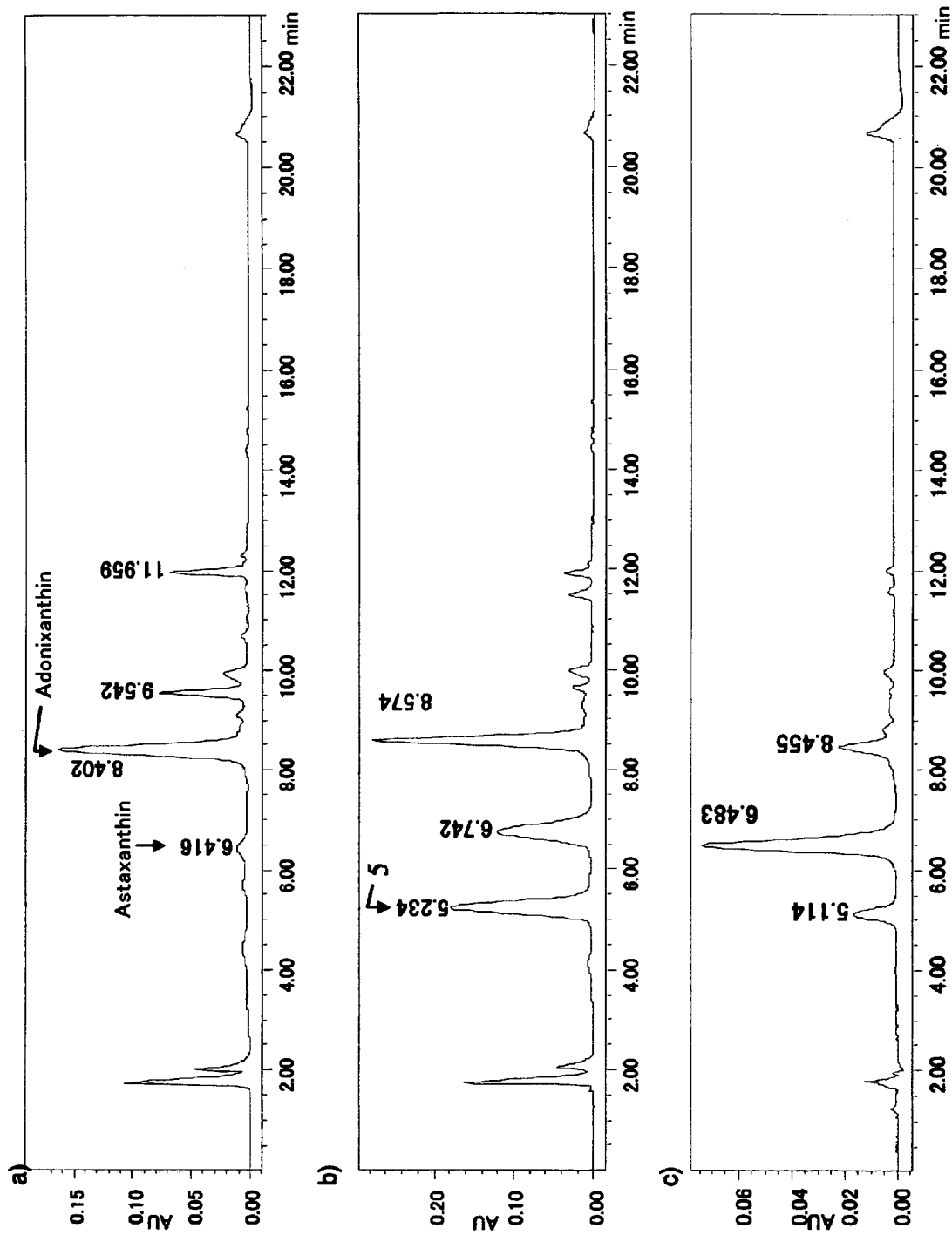
FIG. 9 shows the results of HPLC-PDA analysis using pAC-Asta (plasmid for astaxanthin production)-introduced *E. coli* as a host. a) HPLC chromatogram of pigments produced by pAC-Asta-introduced *E. coli* (470 mn). b) HPLC chromatogram of pigments produced by pUCBre-O11 and pAC-Asta-introduced *E. coli* (470 mn). The peak of a novel pigment is marked with an arrow. Peak 2 was identified as 2,3,2',3'-tetrahydroxy-β,β-carotene-4-one. c) HPLC chromatogram when astaxanthin was added to b) above (470 nm). Peak 5 was identified as 2-hydroxyasataxanthin.

Finally, plasmid pUCBre-O11 (lacZ::SD212-ORF11) was introduced into an *E. coli* clone carrying plasmid pAC-Asta and producing astaxanthin and adonixanthin, and the resultant pigments were analyzed in the same manner as described in Example 11 (FIG. 9). As a result, a peak of astaxanthin was observed at retention time 6.4-6.7 min and a peak of adonixanthin at retention time 8.4-8.6 min. Further, the presence of substance 5 with absorption maximum of 475 nm was observed on more highly polar side than astaxanthin whose retention time is 5.1-5.2 min.; this substance showed a waveform of single-mountain form typical in those carotenoids having keto group(s) in the conjugated system of the β-ionone ring (FIG. 9; marked with an arrow). Carotenoid 5 was identified as 2-hydroxyastaxanthin (see FIG. 2 and Example 13). From the results described so far, it was elucidated that the β-ionone ring-2-hydroxylase (gene product encoded by ORF11) is low (broad) in substrate specificity like other carotenoid biosynthesis enzymes.

EXAMPLE 13

Identification of Pigments Converted by ORF11 (Known Substances)

A pUCBre-O11 and pACCAR25ΔcrtX-introduced *E. coli* clone was cultured in 2 L of 2×YT medium, and cells were harvested by centrifugation at 8,000 rpm for 10 min. The cells were suspended in STE buffer (see Example 3) and centrifuged at 8,000 rpm for 10 min to harvest the cells again. Acetone-methanol (1:1) (400 ml) was added to the cells and agitated for 1 hr. After filtration, the filtrate was vacuum-concentrated to thereby obtain 267 mg of extract, which was then separated by Silica Gel-60 (15 g) column chromatography. Carotenoids were eluted with 100 ml each of hexane-ethyl acetate solvents (8:2) (7:3) (6:4) and (1:1) in succession. As a result, three colored fractions were obtained. One was zeaxanthin. The remaining two fractions were identified by HPLC-PDA-MS analysis and $^1$H-NMR analysis. For HPLC-PDA-MS analysis, Nano Space SI-2 (Shiseido) was used as a semi-micro HPLC system equipped with a PDA (photodiode array) detector. To this system, an ion trapping type mass spectrometer LCQ advantage system (ThermoQuest) was connected. As a column, a Develosil C30-UG-3 (1.0 mm i.d.×150 mm) (Nomura Chemical) which is a C30 column was used. As a pre-column, Develosil C30-UG-S was used. Carotenoids were eluted at a flow rate of 1.0 ml/min with solvent A (96% methanol) for 12 min, then by a gradient from solvent A to solvent B (tert-methyl butyl ether (TMBE)) (B: β-60%, from 12 min to 72 min), and finally eluted under that state from 72 min to 82 min. MS was detected by Atmospheric Pressure Chemical Ionization (APCI). $^1$H-NMR was measured with INOVA750 system (Varian) in deuterated chloroform.

As a result of HPLC-PDA-MS analysis (retention time (RT) 13.48 min; λmax 449, 475 nm; m/z 601 [M+H]$^+$, 583 [M+H—H$_2$O]$^+$, 565[M+H—2H$_2$O]$^+$; and RT 17.75min; λmax 450, 476 nm; m/z 585 [M+H]$^+$, 567 [M+H—H$_2$O]$^+$) and $^1$H-NMR analysis, the carotenoids present in the above-described two fractions were identified as nostoxanthin (2,2'-dihydroxyzeaxanthin) and caloxanthin (2-hydroxyzeaxanthin) (Buchecker, R., Liaaen-Jensen, S., Borch, G., Siegelman, H. W., "Carotenoids of blue-green algae. Part 9. Carotenoids of Anacystis nidulans, structures of caloxanthin and nostoxanthin", Phytochemistry 15, 1015-1018, 1976) (see FIG. 10).

Hereinbelow, the $^1$H-NMR data (6 ppm; in parentheses are number of hydrogen atoms, multiplicity, and coupling constant) are shown. Nostoxanthin: 1.01 (6H, s), 1.14 (6H, s), 1.72 (6H, s), 1.98-1.99 (12H, s), 2.15 (2H, dd, J=17.4, 10.0Hz), 2.4 9(2H, dd, J=17.4, 6.7Hz), 3.33 (2H, d, J=10.0Hz), 3.84 (2H, dt, J=6.7, 10.0Hz), 6.0-6.7 (14H, m); Caloxanthin: 1.01 (3H, s), 1.08 (6H, s), 1.14 (3H, s), 1.49 (1H, t, J=12.0Hz), 1.72 (3H, s), 1.75 (3H, s), 1.80 (1H, m), 1.98-1.99 (12H, s), 2.05 (1H, dd, J=17.4, 10.5Hz), 2.15 (1H, dd, J=17.4, 10.0Hz), 2.40 (IH, dd, J=17.4, 6.3 Hz), 2.49 (1H, dd, J=17.4, 6.7Hz), 3.33 (1H, d, J=10.0 Hz), 3.84 (1H, dt, J=6.7, 10.0 Hz), 4.01 (1H, m), 6.0-6.7 (14H, m).

A pUCBre-O11 and pAC-Asta-introduced *E. coli* clone was cultured in 2 L of 2×YT medium, and cells were harvested by centrifugation at 8,000 rpm for 10 min. The cells were suspended in STE buffer (see Example 3) and centrifuged at 8,000 rpm for 10 min to harvest the cells again. Acetone-methanol (1:1) (400 ml) was added to the cells and agitated for 1 hr. After filtration, the filtrate was vacuum-concentrated to thereby obtain 27 mg of extract, which was then separated by Silica Gel-60 (15 g) column chromatography. Carotenoids were eluted with 100 ml each of hexane-ethyl acetate solvents (7:3) (6:4) and (1:1) in succession. As a result, three colored fractions were obtained. Two were astaxanthin and adonixanthin. The remaining one fraction was identified by HPLC-PDA-MS analysis (RT 11.98 min; λmax 473 nm; m/z 613 [M+H]$^+$) and $^1$H-NMR analysis. As a result, the carotenoid was identified as 2-hydroxyastaxanthin (Non-Patent Document 2) (see FIG. 2). Hereinbelow, the $^1$H-NMR data are shown. 1.22 (3H, s), 1.27 (3H, s), 1.30 (3H, s), 1.33 (3H, s), 1.82 (1H, m), 1.96 (6H, s), 1.98-2.01 (12H, s), 2.17 (1H, bm), 3.53 (1H, m), 4.19 (1H, m), 4.33 (1H, m), 6.2-6.7 (14H, m). Although 2,3,2',3'-tetrahydroxy-β,β-carotene-4,4'-dione (2,2'-dihydroxyastaxanthin) could not be confirmed this time, it is believed that this carotenoid can be obtained by, for example, appropriately selecting culture conditions or the like.

EXAMPLE 14

Identification of Pigments Converted by ORF11 (Novel Substances)

A pUCBre-O11 and pAC-Cantha-introduced *E. coli* clone was cultured in 2 L of 2×YT medium, and cells were harvested by centrifugation at 8,000 rpm for 10 min. The cells were suspended in STE buffer (see Example 3) and centrifuged at 8,000 rpm for 10 min to harvest the cells again. Acetone-methanol (1:1) (400 ml) was added to the cells and agitated for 1 hr. After filtration, the filtrate was vacuum-concentrated to thereby obtain 85 mg of extract, which was then separated by Silica Gel-60 (15 g) column chromatography. Carotenoids were eluted with 100 ml each of hexane-ethyl acetate solvents (8:2) (7:3) and (1:1) in succession. As a result, three colored fractions were obtained. One was canthaxanthin. The remaining two fractions were identified by HPLC-PDA-MS analysis (RT 9.30 min; λmax 472 nm; m/z 597.2 [M+H]$^+$; and RT 17.62 min; λmax 474 nm; m/z 581.2 [M+H]$^+$), high resolution (HR) FABMS analysis, and $^1$H and various two dimensional NMR analyses. As a result, these carotenoids were identified as 2,2'-dihydroxy-β,β-carotene-4,4'-dione (2,2'-dihydroxycanthaxanthin; novel compound (I)) and 2-hydroxy-β,β-carotene-4,4'-dione (2-hydroxycanthaxanthin), respectively (see FIG. 10).

oxygen radicals is the basis for all activities/effects. Therefore, in vitro inhibitory effects of the two carotenoids synthesized in Example 14 on lipid peroxidation caused by free radicals were examined using rat brain homogenate. This assay was conducted basically according to the method of Kubo et al. (Kubo, K., Yoshitake, Y., Kumada, K., Shuto K., Nakamizo, N. "Radical scavenging action of flunarizine in rat brain in vitro". Arch. Int. Pharmacodyn. Ther. 272, 283-295, 1984). Briefly, 0.05 ml of methanol solution of a test sample, 0.1 ml of 1 mM ascorbic acid (final concentration 100 μM) and 0.05 ml of H$_2$O were added to 0.6 ml of 100 mM phosphate buffer (pH 7.4) and pre-incubated at 37° C. for 5 min. Then, 0.2 ml of 2.5% (w/v) rat brain homogenate was added thereto to start reaction, followed by incubation at 37° C. for 1 hr under shaking. One milliliter of a mixed solution con-

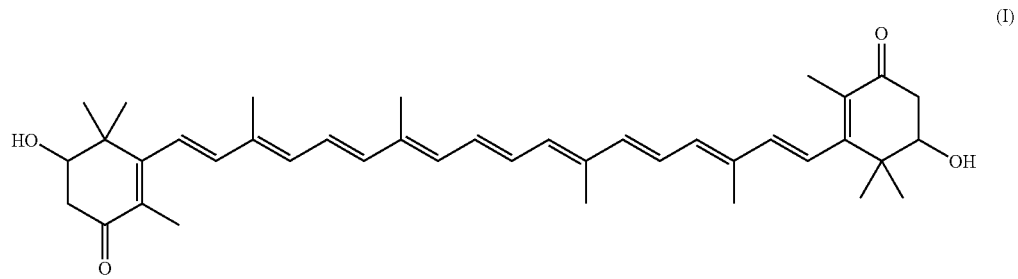

(I)

Hereinafter, HRFABMS analysis data and $^1$H-NMR data are shown. 2,2'-dihydroxy-β, β-carotene-4,4'-dione: HRFABMS (m/z, [M]$^+$), calculated: 596.3866 (C$_{40}$H$_{52}$O$_4$), measured: 596.3863, $^1$H NMR (750 MHz, in deuterated chloroform, δppm), 1.22 (6H, s), 1.26(6H, s), 1.89 (6H, s), 2.00-2.02 (12H, s), 2.62 (2H, dd, J=17.4, 9.0Hz), 2.80 (2H, dd, J=17.4, 4.5Hz), 3.90 (2H, dd, J=9.0, 4.5Hz), 6.2-6.7 (14H, m). 2-hydroxy-β,β-carotene-4,4'-dione: HRFABMS (m/z, [M]$^+$), calculated: 580.3916 (C$_{40}$H$_{52}$O$_3$), measured: 580.3900, $^1$H NMR, 1.21 (6H, s), 1.22 (3H, s), 1.26 (3H, s), 1.85 (2H, t, J=7.0Hz), 1.89 (3H, s), 1.90 (3H, s), 2.00-2.02 (12H, s), 2.51 (2H, t), 2.62 (1H, dd, J=17.4, 9.0Hz), 2.8 (1H, dd, J=17.4, 4.5Hz), 3.90 (1H, dd, J=9.0, 4.5Hz), 6.2-6.7 (14H, m).

2,2'-Dihydroxy-β, β-carotene-4,4'-dione in which a hydroxyl group is introduced at both positions 2 and 2' of canthaxanthin is a novel compound which has not yet been found in nature, as described above. Further, 2-hydroxy-β, β-carotene-4,4'-dione in which a hydroxyl group is introduced at position 2 alone is only reported to have been isolated from a crustacean *Daphinia magna*, and this one produced in the present invention is the first 2-hydroxy-β, β-carotene-4,4'-dione produced by a microorganism (Partali, V., Olsen, Y., Foss, P., Liaaen-Jensen, L., "Carotenoids in food chain studies-I. Zooplankton (*Daphnia magna*) response to a unialgal (*Scenedesmus acutus*) carotenoid diet, to spinach, and to yeast diets supplemented with individual carotenoids", Comp. Biochem. Physiol., 82B(4), 767-772, 1985; Foss, P., Partali, V., Olsen, Y., Borch, G., Liaaen-Jensen, S., "Animal carotnoids 29. New (2R)-2-hydroxy-4-keto-β-type carotenoids from *Daphnia magna* (Crustaceae)", Acta Chemica Scandinavica B40,157-162, 1986).

EXAMPLE 15

Measurement of in vitro Anti-Peroxidation Activity

Although various carotenoids have a wide variety of physiological activities and effects, it is believed that activity to inhibit peroxidation of lipids in the living body caused by taining 20% (w/v) trichloroacetic acid, 0.5% (w/v) 2-thiobarbituric acid and 0.2 N HCl was added to the above reaction solution to terminate the reaction. The resultant solution was boiled at 100 ° C. for 30 min for color development. After cooling, the solution was centrifuged at 3000 rpm for 5 min. Absorbance at 532 nm (A$_{532}$) of the resultant supernatant was measured. The concentration of test sample which is required to decrease the A$_{532}$ of test sample addition group to one half of the A$_{532}$ of test sample non-addition group was calculated as IC$_{50}$. This value was taken as lipid peroxidation inhibitory effect in rat brain homogenate. The results of this experiment are shown in Table 4. As is clear from Table 4, 2-hydroxy-β, β-carotene-4,4'-dione (2-hydroxycanthaxanthin) and 2,2'-dihydroxy-β,β-carotene-4,4'-dione (2,2'-dihydroxycanthaxanthin) have strong inhibitory effects on lipid peroxidation. Especially, the latter (novel substance) exhibited a strong inhibitory effect on lipid peroxidation.

TABLE 4

Inhibitory Effects of Carotenoids with 2-Hydroxyl Group and 4-Keto Group on Lipid Peroxidation in Rat Brain Homogenate

| Carotenoid | IC$_{50}$ (μM) |
|---|---|
| β-Carotene | >100 |
| Canthaxanthin | 50 |
| 2-Hydroxycanthaxanthin | 8.1 |
| 2,2'-Dihydroxycanthaxanthin | 4.8 |

The present specification encompasses the contents disclosed in the specifications and/or drawings of Japanese Patent Applications No. 2003-388165 and No. 2004-165919 based on which the present patent application claims priority. All publications, patents and patent applications cited herein are incorporated herein by reference in their entirety.

The invention claimed is:

1. An isolated peptide selected from the following (a), (b), or (c):
 (a) a peptide consisting of the amino acid sequence as shown in SEQ ID NO: 4;
 (b) a peptide which is isolated from a naturally occurring bacterium and which consists of an amino acid sequence having a 90% or more identity with the amino acid sequence as shown in SEQ ID NO: 4 and has β-ionone ring-2-hydroxylase activity; or
 (c) a peptide which is encoded by a DNA consisting of the nucleotide sequence as shown in SEQ ID NO: 3 or a DNA that hybridizes to the full complement of SEQ ID NO:3 under stringent conditions of about 0.2X SSC, 0.1% SDS, 65° C. and has β-ionone ring-2-hydroxylase activity.

2. An isolated gene encoding a peptide selected from the following (a), (b), or (c):
 (a) a peptide consisting of the amino acid sequence as shown in SEQ ID NO: 4;
 (b) a peptide which is isolated from a naturally occurring bacterium and which consists of an amino acid sequence having a 90% or more identity with the amino acid sequence as shown in SEQ ID NO: 4 and has β-ionone ring-2-hydroxylase activity; or
 (c) a peptide which is encoded by a DNA consisting of the nucleotide sequence as shown in SEQ ID NO: 3 or a DNA that hybridizes to the full complement of SEQ ID NO: 3 under stringent conditions of about 0.2X SSC, 0.1% SDS, 65° C. and has β-ionone ring-2-hydroxylase activity.

3. An isolated microorganism comprising the gene according to claim 2, wherein the microorganism is capable of introducing a hydroxyl group at the position 2 carbon of a β-ionone ring.

4. An isolated microorganism comprising the gene according to claim 2 and other carotenoid biosynthesis genes, wherein the microorganism is capable of introducing a hydroxyl group at the position 2 carbon of a β-ionone ring.

5. The microorganism according to claim 4, wherein the other carotenoid biosynthesis genes are all or a part of a gene cluster required for synthesizing β-ionone ring-containing carotenoids from farnesyl pyrophosphate.

6. The microorganism according to claim 3, wherein the microorganism is *Escherichia coli*.

7. A method of preparing a hydroxylated carotenoid, comprising culturing the microorganism according to claim 3 in a medium and obtaining from the resultant culture or cells a carotenoid which is hydroxylated at the position 2 carbon of its β-ionone ring.

8. The method according to claim 7, wherein the carotenoid which is hydroxylated at the position 2 carbon of its β-ionone ring is β,β-carotene-2-ol (2-hydroxy-β-carotene), β,β-carotene-2,2'-diol (2,2'-dihydroxy-β-carotene), caloxanthin (2-hydroxyzeaxanthin), nostoxanthin (2,2'-dihydroxyzeaxanthin), 2-hydroxy-β,β-carotene-4,4'-dione (2-hydroxycanthaxanthin), 2,2'-dihydroxy-β,β-carotene-4,4'-dione (2,2'-dihydroxycanthaxanthin), 2-hydroxyastaxanthin or 2,3,2',3'-tetrahydroxy-β,β-carotene-4,4'-dione (2,2'-dihydroxyastaxanthin).

9. The isolated microorganism of claim 4, wherein other carotenoid biosynthesis genes is one or more genes selected from the group consisting of crtE encoding an enzyme that synthesizes geranylgeranyl pyrophosphate (GGPP) from farnesyl pyrophosphate (FPP), crtB encoding an enzyme that synthesizes phytoene from two molecules of GGPP, crtI encoding an enzyme that synthesizes lycopene from phytoene, crtY encoding an enzyme that synthesizes β-carotene from lycopene, and crtW encoding β-ionone ring -4-ketolase.

10. An isolated peptide selected from the following (a), (b), or (c):
 (a) a peptide consisting of the amino acid sequence as shown in SEQ ID NO: 4;
 (b) a peptide which is isolated from a naturally occurring bacterium and which consists of an amino acid sequence having 90% or more identity with the amino acid sequence as shown in SEQ ID NO: 4, wherein the bacterium is capable of introducing a hydroxyl group at the position 2 carbon of a β-ionone ring; or
 (c) a peptide which is isolated from a naturally occurring bacterium and which is encoded by a DNA consisting of the nucleotide sequence as shown in SEQ ID NO: 3 or a DNA that hybridizes to the full complement of SEQ ID NO: 3 under stringent conditions of about 0.2X SSC, 0.1% SDS, 65° C., wherein the bacterium is capable of introducing a hydroxyl group at the position 2 carbon of a β-ionone ring.

11. An isolated gene encoding a peptide selected from the following (a), (b), or (c):
   (a) a peptide consisting of the amino acid sequence as shown in SEQ ID NO: 4;
   (b) a peptide which is isolated from a naturally occurring bacterium and which consists of an amino acid sequence having 90% or more identity with the amino acid sequence as shown in SEQ ID NO: 4, wherein the bacterium is capable of introducing a hydroxyl group at the position 2 carbon of a β-ionone ring; or
   (c) a peptide which is isolated from a naturally occurring bacterium and which is encoded by a DNA consisting of the nucleotide sequence as shown in SEQ ID NO: 3 or a DNA that hybridizes to the full complement of SEQ ID NO: 3 under stringent conditions of about 0.2X SSC, 0.1% SDS, 65° C., wherein the bacterium is capable of introducing a hydroxyl group at the position 2 carbon of a β-ionone ring.

* * * * *